US012227554B2

(12) United States Patent
Deniger et al.

(10) Patent No.: US 12,227,554 B2
(45) Date of Patent: Feb. 18, 2025

(54) METHODS FOR SELECTIVELY EXPANDING CELLS EXPRESSING A TCR WITH A MURINE CONSTANT REGION

(71) Applicant: The United States of America, as represented by the Secretary, Department of Health and Human Services, Bethesda, MD (US)

(72) Inventors: Drew C. Deniger, Houston, TX (US); Steven A. Feldman, Redwood City, CA (US); Steven A. Rosenberg, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 873 days.

(21) Appl. No.: 16/652,948

(22) PCT Filed: Sep. 24, 2018

(86) PCT No.: PCT/US2018/052432
§ 371 (c)(1),
(2) Date: Apr. 1, 2020

(87) PCT Pub. No.: WO2019/070435
PCT Pub. Date: Apr. 11, 2019

(65) Prior Publication Data
US 2020/0254018 A1     Aug. 13, 2020

Related U.S. Application Data

(60) Provisional application No. 62/568,339, filed on Oct. 5, 2017.

(51) Int. Cl.
C07K 14/725 (2006.01)
A61K 39/00 (2006.01)
C12N 5/0783 (2010.01)

(52) U.S. Cl.
CPC ...... *C07K 14/7051* (2013.01); *A61K 39/4611* (2023.05); *A61K 39/4632* (2023.05); *A61K 39/464406* (2023.05); *A61K 39/464451* (2023.05); *A61K 39/464491* (2023.05); *C12N 5/0636* (2013.01); *A61K 2239/28* (2023.05); *C12N 2501/2301* (2013.01); *C12N 2501/2307* (2013.01); *C12N 2501/2312* (2013.01); *C12N 2501/2315* (2013.01); *C12N 2501/2321* (2013.01); *C12N 2501/515* (2013.01); *C12N 2510/00* (2013.01)

(58) Field of Classification Search
CPC ............... A61K 35/17; C07K 14/7051; C12N 5/0636; C12N 2501/515; C12N 2510/00
See application file for complete search history.

(56) References Cited

U.S. PATENT DOCUMENTS

| | | | |
|---|---|---|---|
| 8,034,334 B2 | 10/2011 | Dudley et al. | |
| 8,216,565 B2 | 7/2012 | Restifo et al. | |
| 8,383,099 B2 | 2/2013 | Dudley et al. | |
| 8,785,601 B2 | 7/2014 | Rosenberg et al. | |
| 9,487,573 B2 | 11/2016 | Parkhurst et al. | |
| 9,879,065 B2* | 1/2018 | Robbins | A61K 38/1774 |
| 10,174,098 B2* | 1/2019 | Hinrichs | G01N 33/56983 |
| 10,870,687 B2* | 12/2020 | Hinrichs | A61P 1/00 |
| 10,913,785 B2* | 2/2021 | Hinrichs | A61K 35/17 |
| 11,434,272 B2* | 9/2022 | Hinrichs | A61P 35/00 |
| 2005/0214284 A1* | 9/2005 | Price-Schiavi | G01N 33/57492 435/7.2 |
| 2009/0304657 A1* | 12/2009 | Morgan | C07K 14/7051 435/372 |
| 2012/0244133 A1 | 9/2012 | Rosenberg et al. | |
| 2013/0274203 A1 | 10/2013 | Morgan et al. | |
| 2015/0141347 A1 | 5/2015 | Parkhurst et al. | |
| 2016/0152681 A1 | 6/2016 | Hinrichs et al. | |
| 2017/0145070 A1 | 5/2017 | Hinrichs et al. | |

(Continued)

FOREIGN PATENT DOCUMENTS

| | | |
|---|---|---|
| EP | 1 025 854 A1 | 8/2000 |
| JP | H11-512284 A | 10/1999 |

(Continued)

OTHER PUBLICATIONS

Kummer et al. (Immunology Letters 2001 75: 153-158) (Year: 2001).*
Almagro & Fransson, Frontiers in Bioscience 2008; 13:1619-33 ( (Year: 2008).*
LS Columns (Miltenyi Biotec, 2020) (Year: 2020).*
MACS® Cell Separation (Miltenyi Biotec, 2017) (Year: 2017).*
Tran et al. (Science May 9, 2014, 344:641-645) (Year: 2014).*
Cheng et al., "Multiplexed Activation of Endogenous Genes by CRISPR-on, an RNA-guided Transcriptional Activator System," *Cell Res.*, 23(10): 1163-1171 (2013).
Deniger et al., "Sleeping Beauty Transposition of Chimeric Antigen Receptors Targeting Receptor Tyrosine Kinase-Like Orphan Receptor-1 (ROR1) into Diverse Memory T-Cell Populations," *PLoS One*, 10(6): e0128151 (2015).

(Continued)

*Primary Examiner* — Peter J Reddig
(74) *Attorney, Agent, or Firm* — Leydig, Voit & Mayer

(57) ABSTRACT

Disclosed are methods of selectively expanding a number of T cells. The methods may comprise: modifying human T cells to express a TCR, wherein the TCR comprises a murine constant region; producing a population of cells comprising a number of human T cells expressing the TCR and a number of human T cells not expressing the TCR; and culturing the population of cells in the presence of (i) irradiated feeder cells, (ii) one or more cytokines, and (iii) an antibody, or an antigen-binding portion thereof, wherein the antibody has antigenic specificity for the murine constant region of the TCR, so as to selectively expand the number of T cells expressing the TCR over the number of T cells not expressing the TCR. Also disclosed are related populations of cells, pharmaceutical compositions, and methods of treating or preventing cancer.

17 Claims, 28 Drawing Sheets

Specification includes a Sequence Listing.

(56) References Cited

U.S. PATENT DOCUMENTS

2017/0304421 A1 10/2017 Wang et al.
2017/0319674 A1* 11/2017 Kuball ............... C07K 14/7051

FOREIGN PATENT DOCUMENTS

| JP | 2008-253267 A | 10/2008 |
|---|---|---|
| WO | WO 93/11794 A1 | 6/1993 |
| WO | WO 97/09419 A1 | 3/1997 |
| WO | WO 2016/053339 A1 | 4/2016 |
| WO | WO 2016/079333 A1 | 5/2016 |
| WO | WO 2017/048593 A1 | 3/2017 |
| WO | WO 2017/189254 A1 | 11/2017 |
| WO | WO 2018/026691 A1 | 2/2018 |

OTHER PUBLICATIONS

Deniger et al., "Stable, Nonviral Expression of Mutated Tumor Neoantigen-specific T-cell Receptors Using the Sleeping Beauty Transposon/Transposase System," *Mol. Ther.*, 24(6): 1078-1089 (2016).
Dudley et al., "Generation of Tumor-Infiltrating Lymphocyte Cultures for Use in Adoptive Transfer Therapy for Melanoma Patients," *J. Immunother.*, 26(4): 332-342 (2003).
Field et al., "Comparison of Lentiviral and Sleeping Beauty Mediated αβ T Cell Receptor Gene Transfer," *PLoS One*, 8(6): e68201 (2013).
Grégoire et al., "Engineered Secreted T-cell Receptor Alpha Beta Heterodimers," *Proc Natl Acad Sci USA*, 88(18):8077-8081 (1991).
International Bureau, International Search Report and Written Opinion in International Application No. PCT/US2018/052432, mailed Jan. 11, 2019.
Ivics et al., "Sleeping Beauty transposon mutagenesis in rat spermatogonial stem cells," *Nature Protocols*, 6: 1521-1535 (2011).
Kubo et al., "Characterization of a monoclonal antibody which detects all murine alpha beta T cell receptors," *J. Immunol.*, 142(8): 2736-2742 (1989).
National Library of Medicine, National Center for Biotechnology Information, Protein Database, "1NFD: An Alpha-beta T Cell Receptor (tcr) Heterodimer in Complex With an Anti-tor Fab Fragment Derived From a Mitogenic Antibody," Accession No. 1NFD, deposited on Aug. 4, 1997, updated Nov. 1998. Available online at <ncbi.nlm.nih.gov/Structure/pdb/1NFD>.
National Library of Medicine, National Center for Biotechnology Information, Protein Database, "Chain A, N15 Alpha-beta T-cell Receptor," Accession No. 1NFD_A, deposited on Aug. 4, 1997. Available online at <ncbi.nlm.nih.gov/protein/1NFD_A>.
National Library of Medicine, National Center for Biotechnology Information, Protein Database, "Chain B, N15 Alpha-beta T-cell Receptor," Accession No. 1NFD_B, deposited on Aug. 4, 1997. Available online at <ncbi.nlm.nih.gov/protein/1NFD_B>.
National Library of Medicine, National Center for Biotechnology Information, Protein Database, "Chain C, N15 Alpha-beta T-cell Receptor," Accession No. 1NFD_C, deposited on Aug. 4, 1997. Available online at <ncbi.nlm.nih.gov/protein/1NFD_C>.
National Library of Medicine, National Center for Biotechnology Information, Protein Database, "Chain D, N15 Alpha-beta T-cell Receptor," Accession No. 1NFD_D, deposited on Aug. 4, 1997. Available online at <ncbi.nlm.nih.gov/protein/1NFD_D>.
National Library of Medicine, National Center for Biotechnology Information, Protein Database, "Chain E, H57 Fab," Accession No. 1NFD_E, deposited on Aug. 4, 1997. Available online at <ncbi.nlm.nih.gov/protein/1NFD_E>.
National Library of Medicine, National Center for Biotechnology Information, Protein Database, "Chain F, H57 Fab," Accession No. 1NFD_F, deposited on Aug. 4, 1997. Available online at <ncbi.nlm.nih.gov/protein/1NFD_F>.
National Library of Medicine, National Center for Biotechnology Information, Protein Database, "Chain G, H57 Fab," Accession No. 1NFD_G, deposited on Aug. 4, 1997. Available online at <ncbi.nlm.nih.gov/protein/1NFD_G>.
National Library of Medicine, National Center for Biotechnology Information, Protein Database, "Chain H, H57 Fab," Accession No. 1NFD_H, deposited on Aug. 4, 1997. Available online at <ncbi.nlm.nih.gov/protein/1NFD_H>.
Paul et al., "Tumor gene therapy by MVA-mediated expression of T-cell-stimulating antibodies," *Cancer Gene. Ther.*, 9(5): 470-477 (2002).
"PE anti-mouse TCR β Antibody," BioLegend Technical Data Sheet, accessed online at <biolegend.com/de-at/products/pe-anti-mouse-tcr-beta-chain-antibody-272> on Aug. 7, 2017, updated Feb. 8, 2014.
PÉRez-Mancera et al., "The Deubiquitinase USP9X Suppresses Pancreatic Ductal Adenocarcinoma," *Nature*, 486(7402): 266-270 (2012).
Riddell et al., "The Use of anti-CD3 and anti-CD28 Monoclonal Antibodies to Clone and Expand Human Antigen-Specific T Cells," *J. Immunol. Methods*, 128(2): 189-201 (1990).
Robbins et al., "Mining Exomic Sequencing Data to Identify Mutated Antigens Recognized by Adoptively Transferred Tumor-reactive T cells," *Nat. Med.*, 19(6): 747-752 (2013).
Schrum et al., "Physical and Functional Bivalency Observed Among TCR/CD3 Complexes Isolated from Primary T Cells," *J. Immunol.*, 187(2): 870-878 (2011).
Singh et al., "Reprogramming CD19-specific T cells with IL-21 signaling can improve adoptive immunotherapy of B-lineage malignancies," *Cancer Res.*, 71(10): 3516-3527 (2011).
Tran et al., "Immunogenicity of Somatic Mutations in Human Gastrointestinal Cancers," *Science*, 350(6266): 1387-1390 (2015).
Wang et al., "Atomic Structure of an Alphabeta T Cell Receptor (TCR) Heterodimer in Complex With an anti-TCR Fab Fragment Derived From a Mitogenic Antibody," *EMBO J.*, 17(1): 10-26 (1998).

* cited by examiner

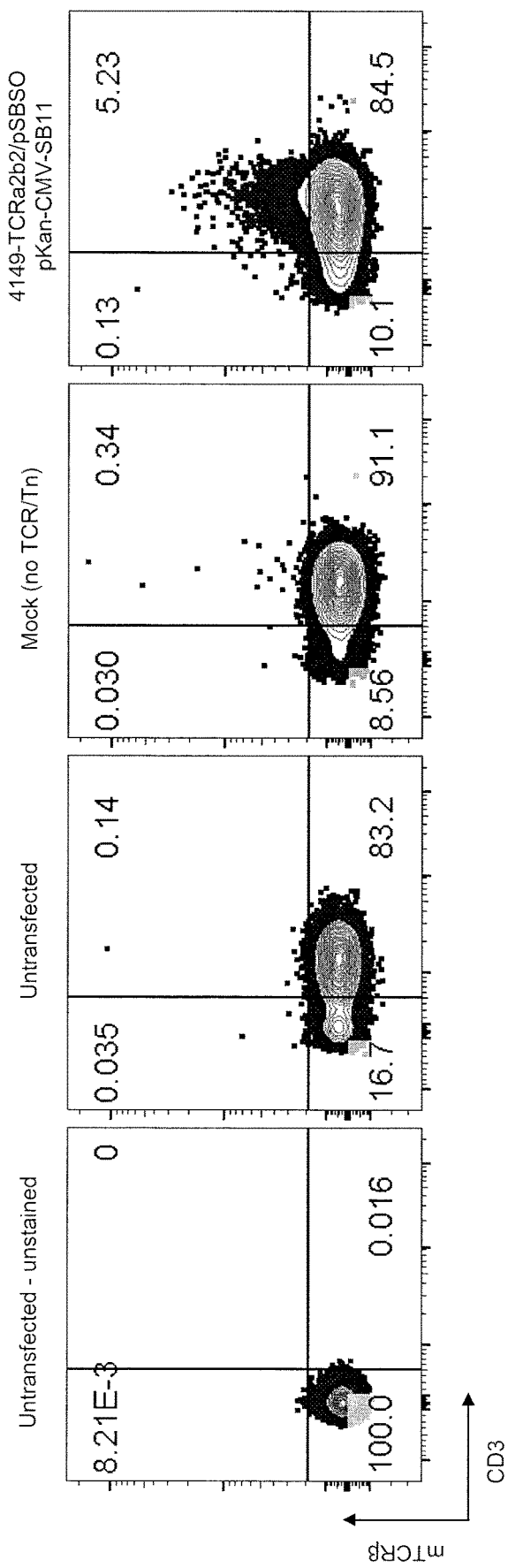

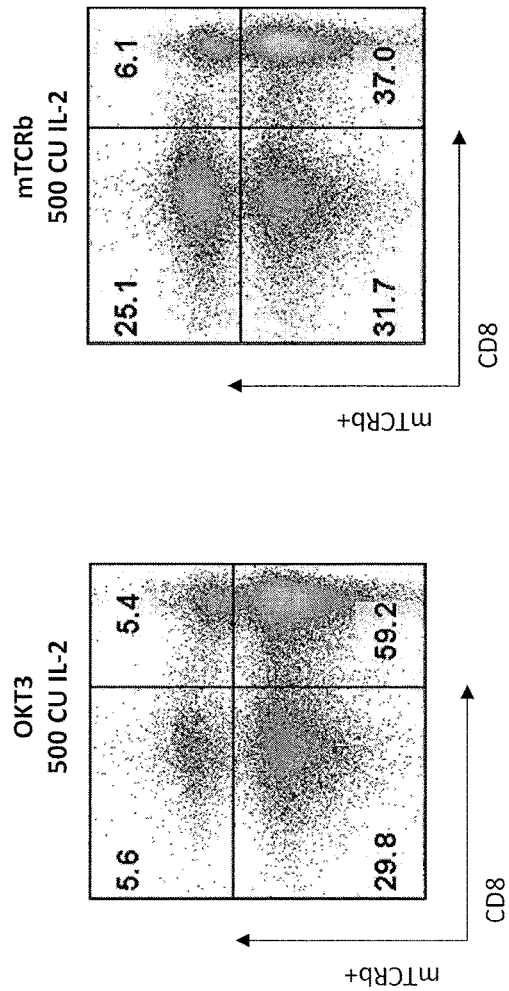
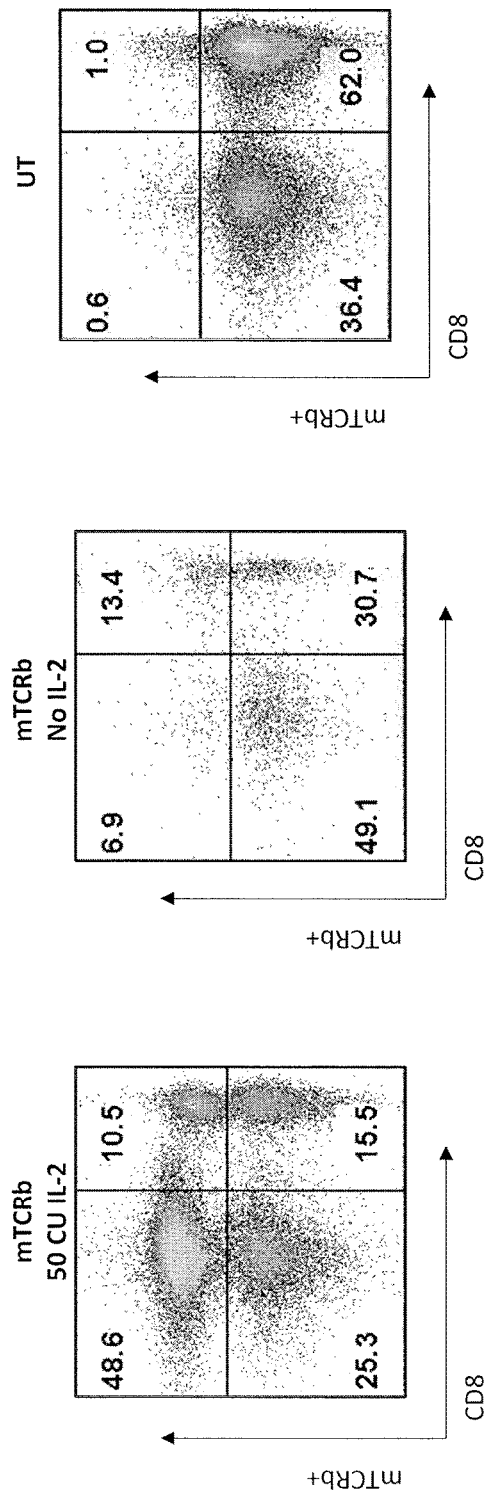
FIG. 12A
FIG. 12B
FIG. 12C
FIG. 12D
FIG. 12E

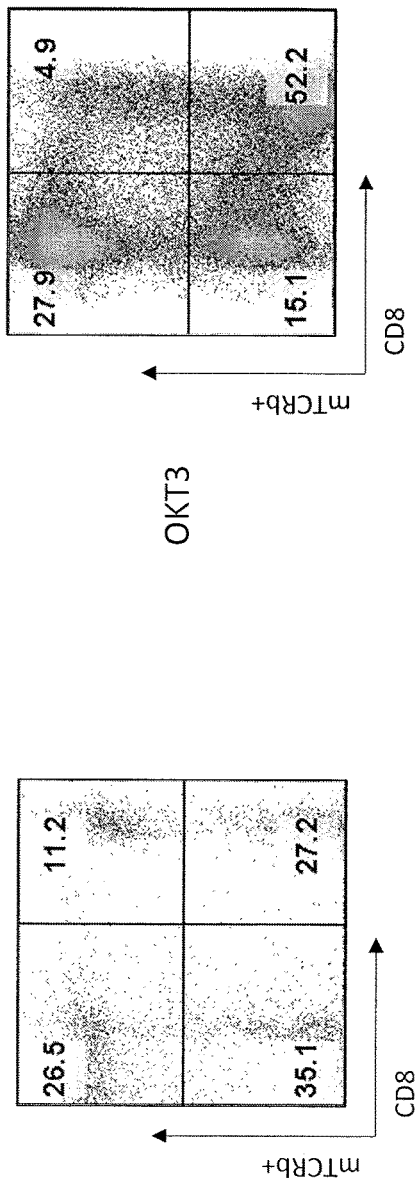
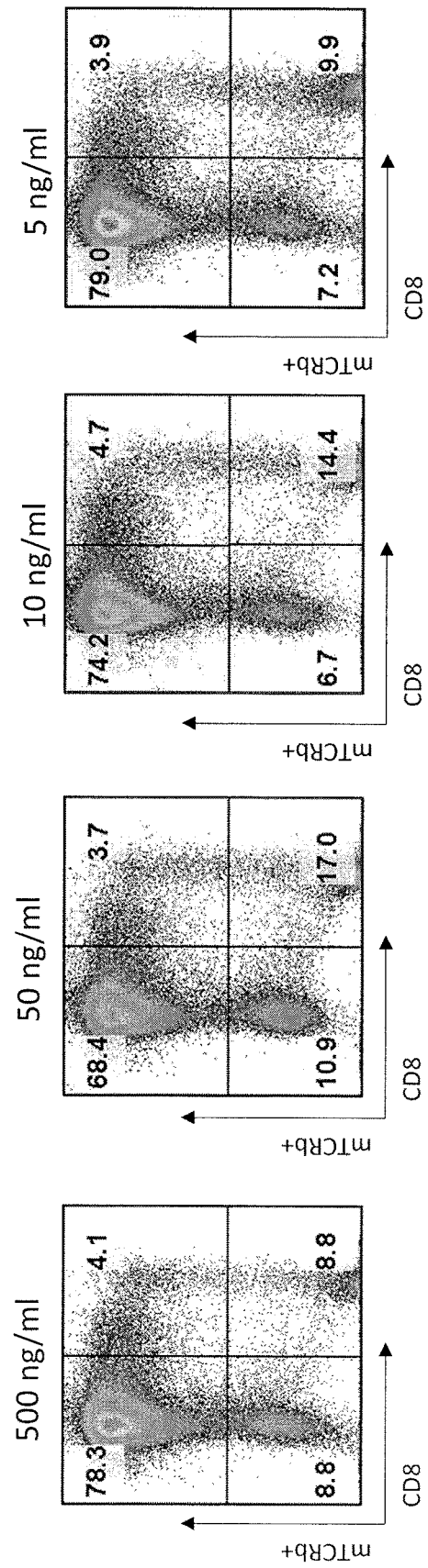
FIG. 14A, FIG. 14B, FIG. 14C, FIG. 14D, FIG. 14E, FIG. 14F

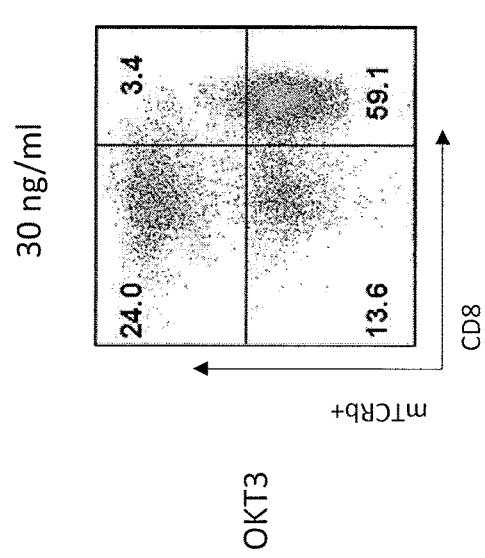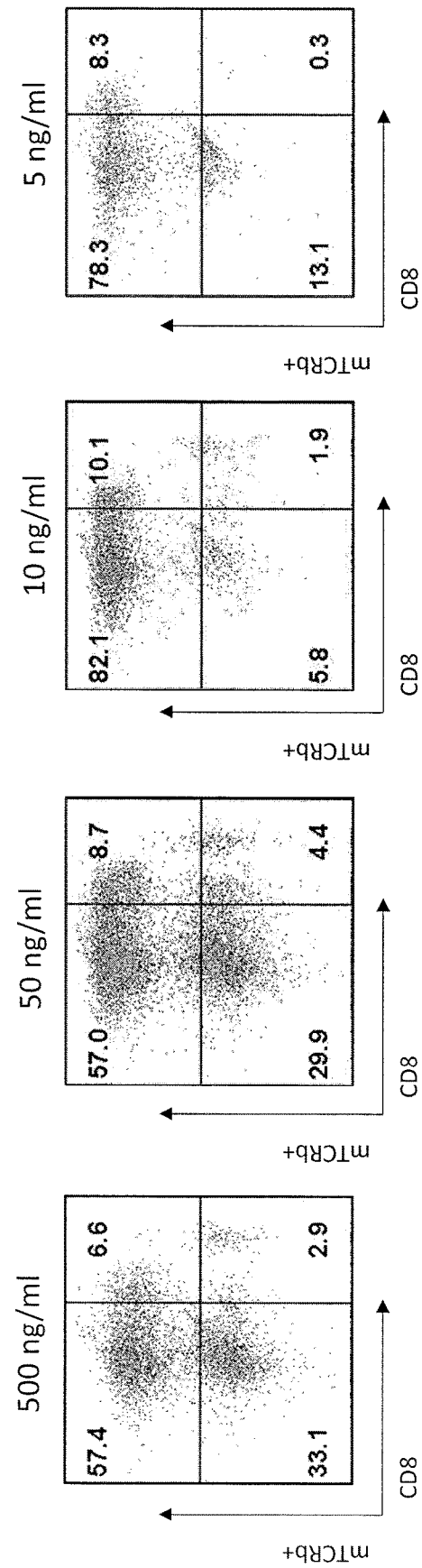
FIG. 16A  FIG. 16B  FIG. 16C  FIG. 16D  FIG. 16E

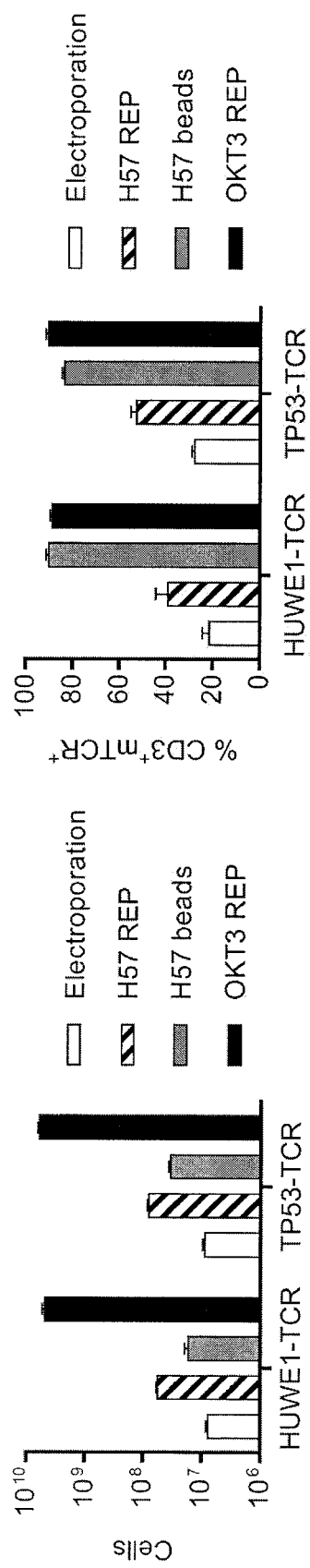
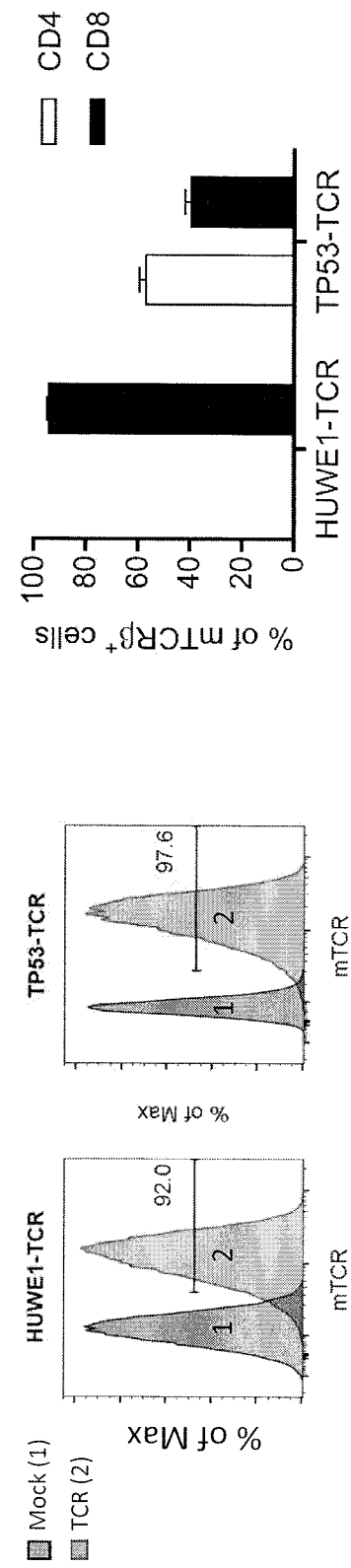
FIG. 23A
FIG. 23B
FIG. 23C
FIG. 23D
FIG. 23E

SEQUENCE LISTING

<160> NUMBER OF SEQ ID NOS: 6

<210> SEQ ID NO 1
<211> LENGTH: 173

```
<212> TYPE: PRT
<213> ORGANISM: Mus musculus

<400> SEQUENCE: 1

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65              70                  75                  80

Thr Phe Trp His Asn Pro Arg Asn His Phe Arg Cys Gln Val Gln Phe
            85                  90                  95

His Gly Leu Ser Glu Glu Asp Lys Trp Pro Glu Gly Ser Pro Lys Pro
        100                 105                 110

Val Thr Gln Asn Ile Ser Ala Glu Ala Trp Gly Arg Ala Asp Cys Gly
    115                 120                 125

Ile Thr Ser Ala Ser Tyr Gln Gln Gly Val Leu Ser Ala Thr Ile Leu
130             135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 2
<211> LENGTH: 109
<212> TYPE: PRT
<213> ORGANISM: Mus musculus

<400> SEQUENCE: 2

Asp Leu Arg Asn Val Thr Pro Pro Lys Val Ser Leu Phe Glu Pro Ser
1               5                   10                  15

Lys Ala Glu Ile Ala Asn Lys Gln Lys Ala Thr Leu Val Cys Leu Ala
            20                  25                  30

Arg Gly Phe Phe Pro Asp His Val Glu Leu Ser Trp Trp Val Asn Gly
        35                  40                  45

Lys Glu Val His Ser Gly Val Ser Thr Asp Pro Gln Ala Tyr Lys Glu
    50                  55                  60

Ser Asn Tyr Ser Tyr Cys Leu Ser Ser Arg Leu Arg Val Ser Ala Thr
65              70                  75                  80

Phe Trp His Asn Pro Arg Asn His Phe Arg Cys Gln Val Gln Phe His
            85                  90                  95

Gly Leu Ser Glu Glu Asp Lys Trp Pro Glu Gly Ser Pro
        100                 105

<210> SEQ ID NO 3
<211> LENGTH: 121
<212> TYPE: PRT
<213> ORGANISM: Armenian hamster

<400> SEQUENCE: 3

Glu Val Tyr Leu Val Glu Ser Gly Gly Asp Leu Val Gln Pro Gly Ser
1               5                   10                  15
```

Ser Leu Lys Val Ser Cys Ala Ala Ser Gly Phe Thr Phe Ser Asp Phe
            20                  25                  30

Trp Met Tyr Trp Val Arg Gln Ala Pro Gly Lys Gly Leu Glu Trp Val
        35                  40                  45

Gly Arg Ile Lys Asn Ile Pro Asn Asn Tyr Ala Thr Glu Tyr Ala Asp
50                  55                  60

Ser Val Arg Gly Arg Phe Thr Ile Ser Arg Asp Asp Ser Arg Asn Ser
65                  70                  75                  80

Ile Tyr Leu Gln Met Asn Arg Leu Arg Val Asp Asp Thr Ala Ile Tyr
                85                  90                  95

Tyr Cys Thr Arg Ala Gly Arg Phe Asp His Phe Asp Tyr Trp Gly Gln
            100                 105                 110

Gly Thr Met Val Thr Val Ser Ser Ala
            115                 120

<210> SEQ ID NO 4
<211> LENGTH: 110
<212> TYPE: PRT
<213> ORGANISM: Armenian hamster

<400> SEQUENCE: 4

Tyr Glu Leu Ile Gln Pro Ser Ser Ala Ser Val Thr Val Gly Glu Thr
1               5                   10                  15

Val Lys Ile Thr Cys Ser Gly Asp Gln Leu Pro Lys Asn Phe Ala Tyr
            20                  25                  30

Trp Phe Gln Gln Lys Ser Asp Lys Asn Ile Leu Leu Leu Ile Tyr Met
        35                  40                  45

Asp Asn Lys Arg Pro Ser Gly Ile Pro Glu Arg Phe Ser Gly Ser Thr
50                  55                  60

Ser Gly Thr Thr Ala Thr Leu Thr Ile Ser Gly Ala Gln Pro Glu Asp
65                  70                  75                  80

Glu Ala Ala Tyr Tyr Cys Leu Ser Ser Tyr Gly Asp Asn Asn Asp Leu
                85                  90                  95

Val Phe Gly Ser Gly Thr Gln Leu Thr Val Leu Arg Gly Pro
            100                 105                 110

<210> SEQ ID NO 5
<211> LENGTH: 222
<212> TYPE: PRT
<213> ORGANISM: Armenian hamster

<400> SEQUENCE: 5

Glu Val Tyr Leu Val Glu Ser Gly Gly Asp Leu Val Gln Pro Gly Ser
1               5                   10                  15

Ser Leu Lys Val Ser Cys Ala Ala Ser Gly Phe Thr Phe Ser Asp Phe
            20                  25                  30

Trp Met Tyr Trp Val Arg Gln Ala Pro Gly Lys Gly Leu Glu Trp Val
        35                  40                  45

Gly Arg Ile Lys Asn Ile Pro Asn Asn Tyr Ala Thr Glu Tyr Ala Asp
50                  55                  60

Ser Val Arg Gly Arg Phe Thr Ile Ser Arg Asp Asp Ser Arg Asn Ser
65                  70                  75                  80

Ile Tyr Leu Gln Met Asn Arg Leu Arg Val Asp Asp Thr Ala Ile Tyr
                85                  90                  95

Tyr Cys Thr Arg Ala Gly Arg Phe Asp His Phe Asp Tyr Trp Gly Gln
            100                 105                 110

```
Gly Thr Met Val Thr Val Ser Ser Ala Thr Thr Ala Pro Ser Val
        115                 120                 125

Tyr Pro Leu Ala Pro Ala Cys Asp Ser Thr Thr Ser Thr Thr Asp Thr
    130                 135                 140

Val Thr Leu Gly Cys Leu Val Lys Gly Tyr Phe Pro Glu Pro Val Thr
145                 150                 155                 160

Val Ser Trp Asn Ser Gly Ala Leu Thr Ser Gly Val His Thr Phe Pro
                165                 170                 175

Ser Val Leu His Ser Gly Leu Tyr Ser Leu Ser Ser Val Thr Val
                180                 185                 190

Pro Ser Ser Thr Trp Pro Lys Gln Pro Ile Thr Cys Asn Val Ala His
            195                 200                 205

Pro Ala Ser Ser Thr Lys Val Asp Lys Lys Ile Glu Pro Arg
    210                 215                 220

<210> SEQ ID NO 6
<211> LENGTH: 212
<212> TYPE: PRT
<213> ORGANISM: Armenian hamster

<400> SEQUENCE: 6

Tyr Glu Leu Ile Gln Pro Ser Ser Ala Ser Val Thr Val Gly Glu Thr
1               5                   10                  15

Val Lys Ile Thr Cys Ser Gly Asp Gln Leu Pro Lys Asn Phe Ala Tyr
                20                  25                  30

Trp Phe Gln Gln Lys Ser Asp Lys Asn Ile Leu Leu Leu Ile Tyr Met
            35                  40                  45

Asp Asn Lys Arg Pro Ser Gly Ile Pro Glu Arg Phe Ser Gly Ser Thr
        50                  55                  60

Ser Gly Thr Thr Ala Thr Leu Thr Ile Ser Gly Ala Gln Pro Glu Asp
65                  70                  75                  80

Glu Ala Ala Tyr Tyr Cys Leu Ser Ser Tyr Gly Asp Asn Asn Asp Leu
                85                  90                  95

Val Phe Gly Ser Gly Thr Gln Leu Thr Val Leu Arg Gly Pro Lys Ser
                100                 105                 110

Ser Pro Lys Val Thr Val Phe Pro Pro Ser Pro Glu Glu Leu Arg Thr
            115                 120                 125

Asn Lys Ala Thr Leu Val Cys Leu Val Asn Asp Phe Tyr Pro Gly Ser
        130                 135                 140

Ala Thr Val Thr Trp Lys Ala Asn Gly Ala Thr Ile Asn Asp Gly Val
145                 150                 155                 160

Lys Thr Thr Lys Pro Ser Lys Gln Gly Gln Asn Tyr Met Thr Ser Ser
                165                 170                 175

Tyr Leu Ser Leu Thr Ala Asp Gln Trp Lys Ser His Asn Arg Val Ser
                180                 185                 190

Cys Gln Val Thr His Glu Gly Glu Thr Val Glu Lys Ser Leu Ser Pro
            195                 200                 205

Ala Glu Cys Leu
    210
```

METHODS FOR SELECTIVELY EXPANDING CELLS EXPRESSING A TCR WITH A MURINE CONSTANT REGION

CROSS-REFERENCE TO RELATED APPLICATIONS

This patent application is the U.S. national stage of PCT/US2018/052432, filed Sep. 24, 2018, which claims the benefit of U.S. Provisional Patent Application No. 62/568,339, filed Oct. 5, 2017, which is incorporated by reference in its entirety herein.

STATEMENT REGARDING FEDERALLY SPONSORED RESEARCH OR DEVELOPMENT

This invention was made with Government support under project number Z1A BC 010985 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 8,923 Byte ASCII (Text) file named "748366_ST25.txt" dated Apr. 1, 2020.

BACKGROUND OF THE INVENTION

The treatment of cancer by administering cells which have been modified to express an exogenous T cell receptor (TCR) has produced positive clinical results in some patients. Nevertheless, obstacles to the more widespread success of such therapies remain. For example, a low efficiency of the delivery of the gene encoding the exogenous TCR may result in low numbers of cells expressing the exogenous TCR. Accordingly, there exists an unmet need for improved methods of producing cells which express an exogenous TCR.

BRIEF SUMMARY OF THE INVENTION

An embodiment of the invention provides a method of selectively expanding a number of T cells, the method comprising: modifying human T cells to express a TCR, wherein the TCR comprises a murine constant region; producing a population of cells comprising a number of human T cells expressing the TCR and a number of human T cells not expressing the TCR; and culturing the population of cells in the presence of (i) irradiated feeder cells, (ii) one or more cytokines, and (iii) an antibody, or an antigen-binding portion thereof, wherein the antibody has antigenic specificity for the murine constant region of the TCR, so as to selectively expand the number of T cells expressing the TCR over the number of T cells not expressing the TCR.

Further embodiments of the invention provide related populations of cells comprising a selectively expanded number of T cells prepared according to the inventive methods and pharmaceutical compositions comprising the population of cells.

Still another embodiment of the invention provides methods of method of treating or preventing cancer in a mammal, the method comprising selectively expanding a number of T cells according to the inventive method and administering the selectively expanded number of T cells to the mammal in an amount effective to treat or prevent cancer in the mammal.

BRIEF DESCRIPTION OF THE SEVERAL VIEWS OF THE DRAWING(S)

Figure 2:
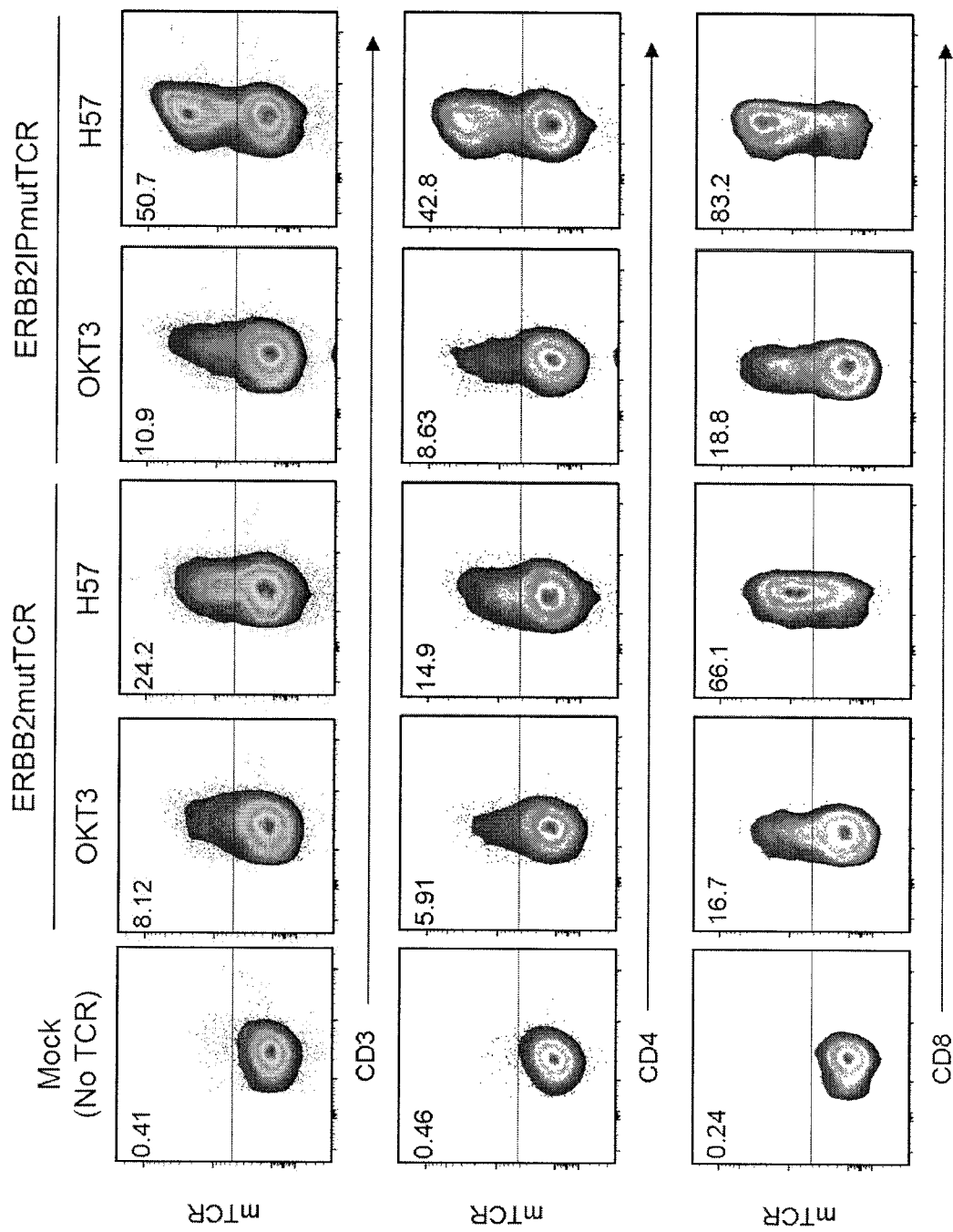

FIG. 2 shows experimental data (dot plots) illustrating (i) CD3, CD4, or CD8 expression and (ii) mTCRβ expression detected by FACS in anti-mutated ERBB2 mTCR or anti-mutated ERBB2IP mTCR-electroporated cells (ERBB2mutTCR or ERBB2IPmutTCR) which underwent a standard rapid expansion protocol (REP) using OKT3 Ab or selective expansion using H57 Ab. T cells electroporated with electroporation buffer only (mock; no DNA/TCR) served as a negative control. The numbers in the dot plots are the percentages of mTCR$^+$ cells detected.

Figure 3A:
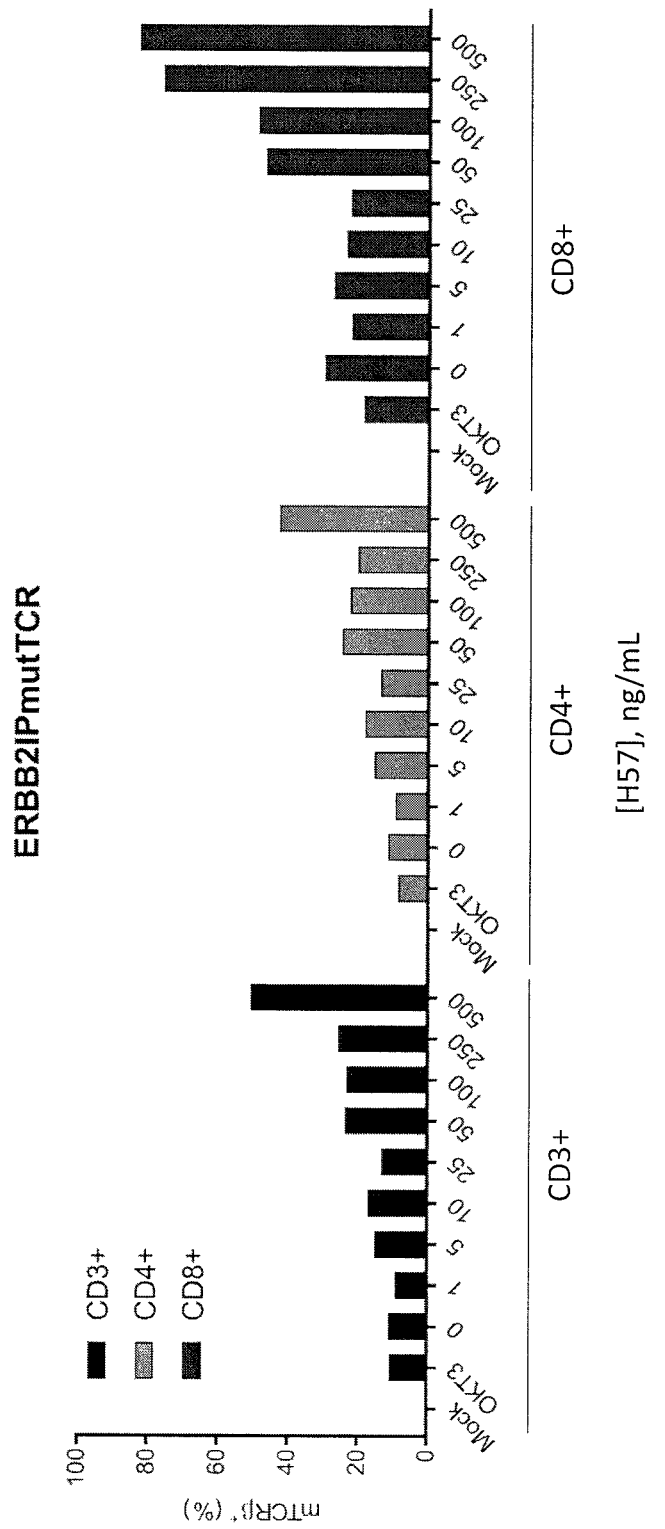
Figure 3B:
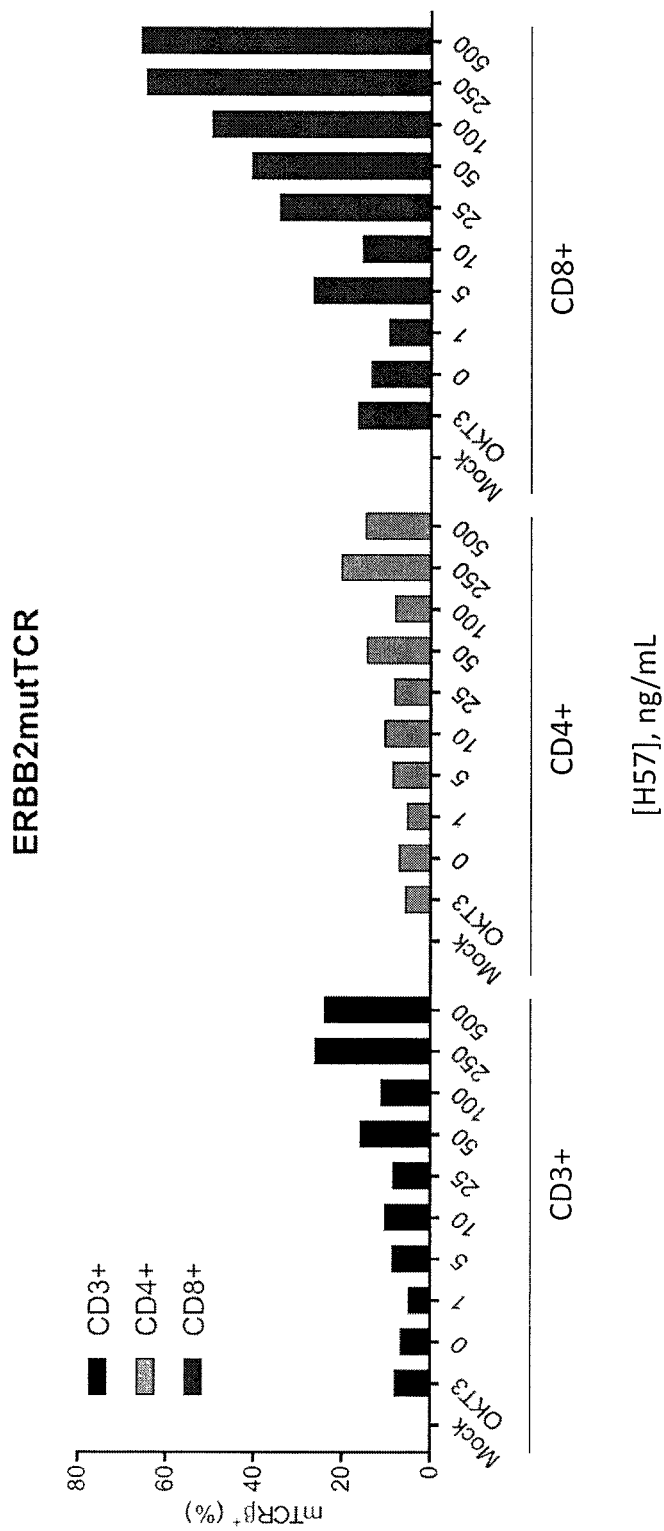

FIGS. 3A and 3B are graphs showing the percentage (%) of anti-mutated ERBB2IP mTCRβ$^+$ (ERBB2IPmutTCR) (A) or anti-mutated ERBB2 (ERBB2mutTCR) mTCRβ$^+$ (B) cells also expressing CD3, CD4, or CD8 detected following selective expansion with various concentrations (ng/mL) of the H57 Ab. T cells electroporated with electroporation buffer only (mock; no DNA/TCR) served as a negative control. Electroporated cells which underwent standard REP with OKT3 Ab instead of selective expansion with H57 Ab served as a positive control for non-specific T cell growth.

Figure 4A:
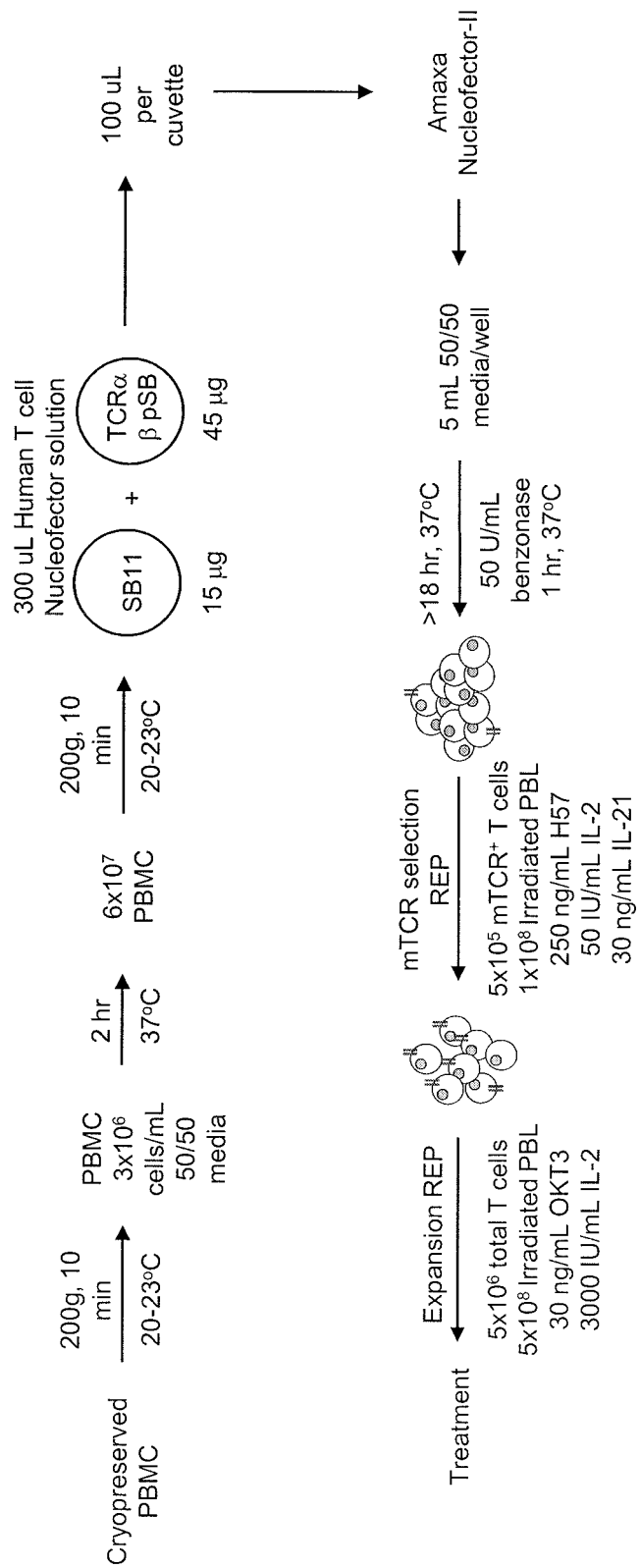

FIG. 4A is a schematic illustrating a method of selectively expanding the number of T cells expressing a TCR comprising a murine constant region (mTCR) in accordance with an embodiment of the invention.

Figure 4B:
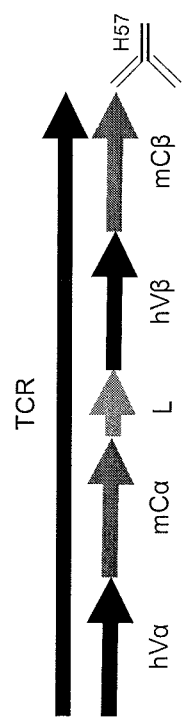

FIG. 4B is a schematic illustrating the binding of the H57 Ab to the murine TCR β chain constant region (mCβ) of a TCR. The other components of the TCR include a human TCR α chain variable region (hVα), a murine TCR α chain constant region (mCα), a synthetic linker sequence (L), and a human TCR β chain variable region (hVβ).

FIGS. 5A-5D show experimental data (dot plots) illustrating CD3 expression and murine TCR β chain (mTCRβ) expression detected by FACS in untransfected, unstained cells (A), untransfected, stained cells (B), cells electroporated with electroporation buffer only (Mock) (no TCR/transposon (Tn)) (C), and cells electroporated with the SBTS plasmid encoding the mTCR (4149-TCRa2b2/pSBSO) and the SBTS plasmid encoding transposase described in Example 3 (pKan-CMV-SB11) (D). The numbers in the dot plots are the percentages of CD3$^+$/mTCRβ$^+$ (upper right quadrant), CD3$^+$/mTCRβ$^-$ (lower right quadrant), CD3$^-$/mTCRβ$^-$ (lower left quadrant), and CD3$^-$/mTCRβ$^+$ cells (upper left quadrant).

Figure 6:
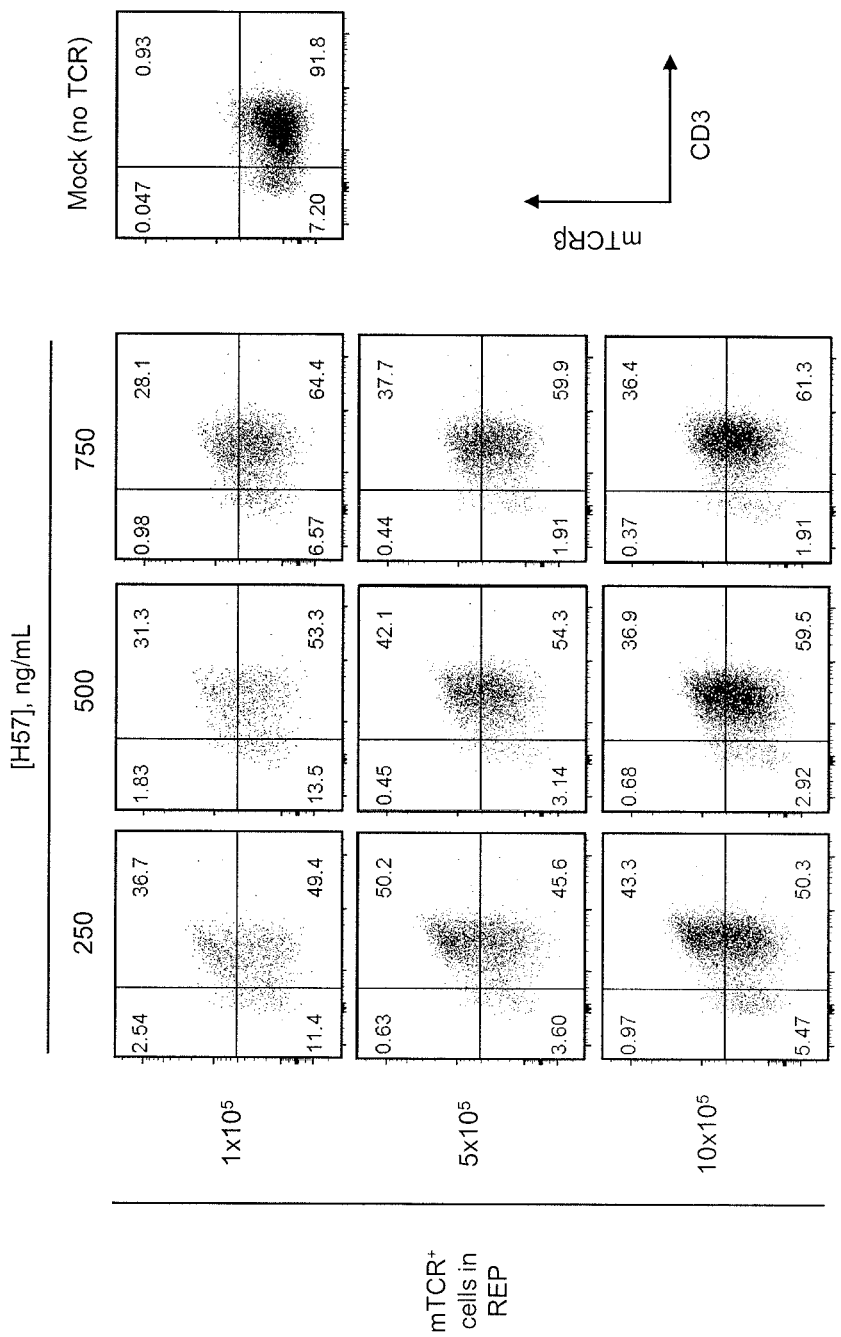

FIG. 6 shows experimental data (dot plots) illustrating CD3 expression and mTCRβ expression detected by FACS in mTCR-electroporated cells which underwent selective expansion at the indicated initial number of electroporated cells (mTCR$^+$ cells in REP with the indicated concentrations of H57 Ab (ng/mL). Cells electroporated with electroporation buffer only (Mock) (no TCR) served as a negative control. The numbers in the dot plots are the percentages of CD3$^+$/mTCRβ$^+$ (upper right quadrant), CD3$^+$/mTCRβ$^-$ (lower right quadrant), CD3⁻/mTCRβ⁻ (lower left quadrant), and CD3⁻/mTCRβ⁺ cells (upper left quadrant).

Figure 7:
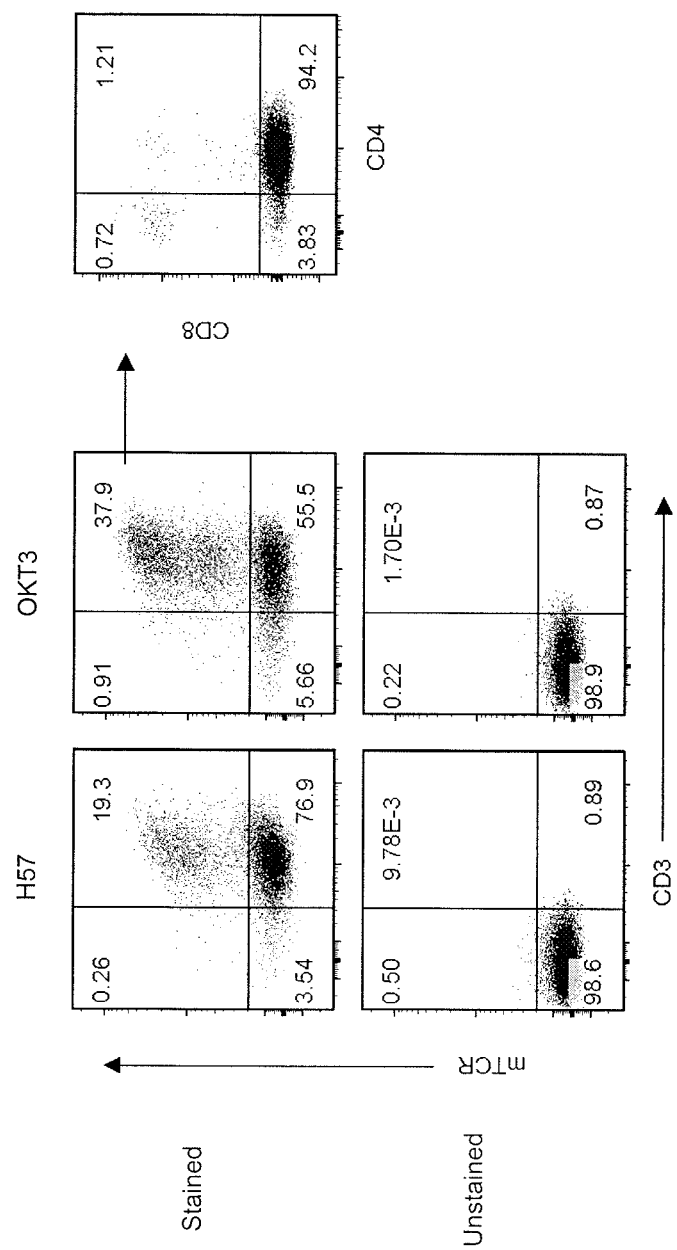

FIG. 7 shows experimental data (dot plots) illustrating CD3 expression and mTCRβ expression detected by FACS in mTCR-electroporated cells which underwent a second expansion with H57 Ab or OKT3 Ab and which were stained or unstained. Also shown are experimental data (dot plot) illustrating CD4 and CD8 expression detected by FACS in mTCR-electroporated cells which underwent the second expansion with OKT3 Ab.

Figures 8A, 8B, 8C:
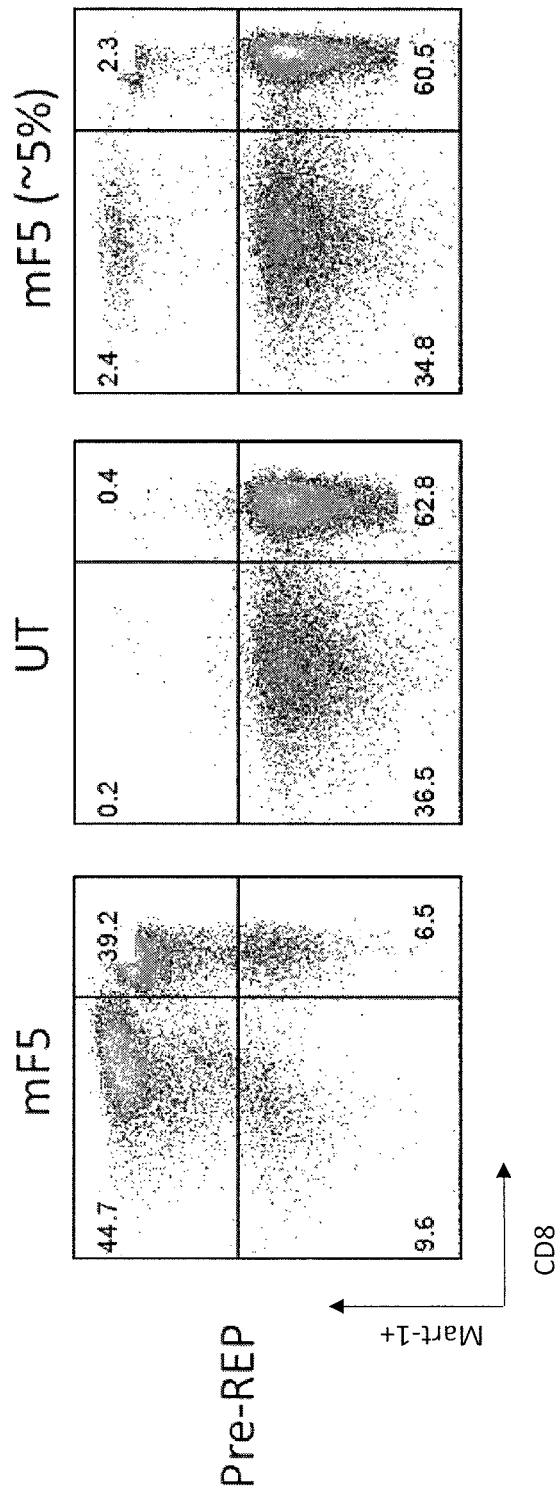

FIGS. 8A and 8B show experimental data (dot plots) illustrating CD8 expression and anti-MART-1 TCR expression detected by FACS for untransduced (UT) (FIG. 8B) and transduced (FIG. 8A) cells prior to expansion (pre-rapid expansion protocol (REP)).

FIG. 8C shows experimental data (dot plot) illustrating CD8 expression and anti-MART-1 TCR expression detected by FACS for the transduced cells of FIG. 8A prior to expansion (pre-REP) and following dilution to approximately 5% mTCRb+ cells.

Figure 9:
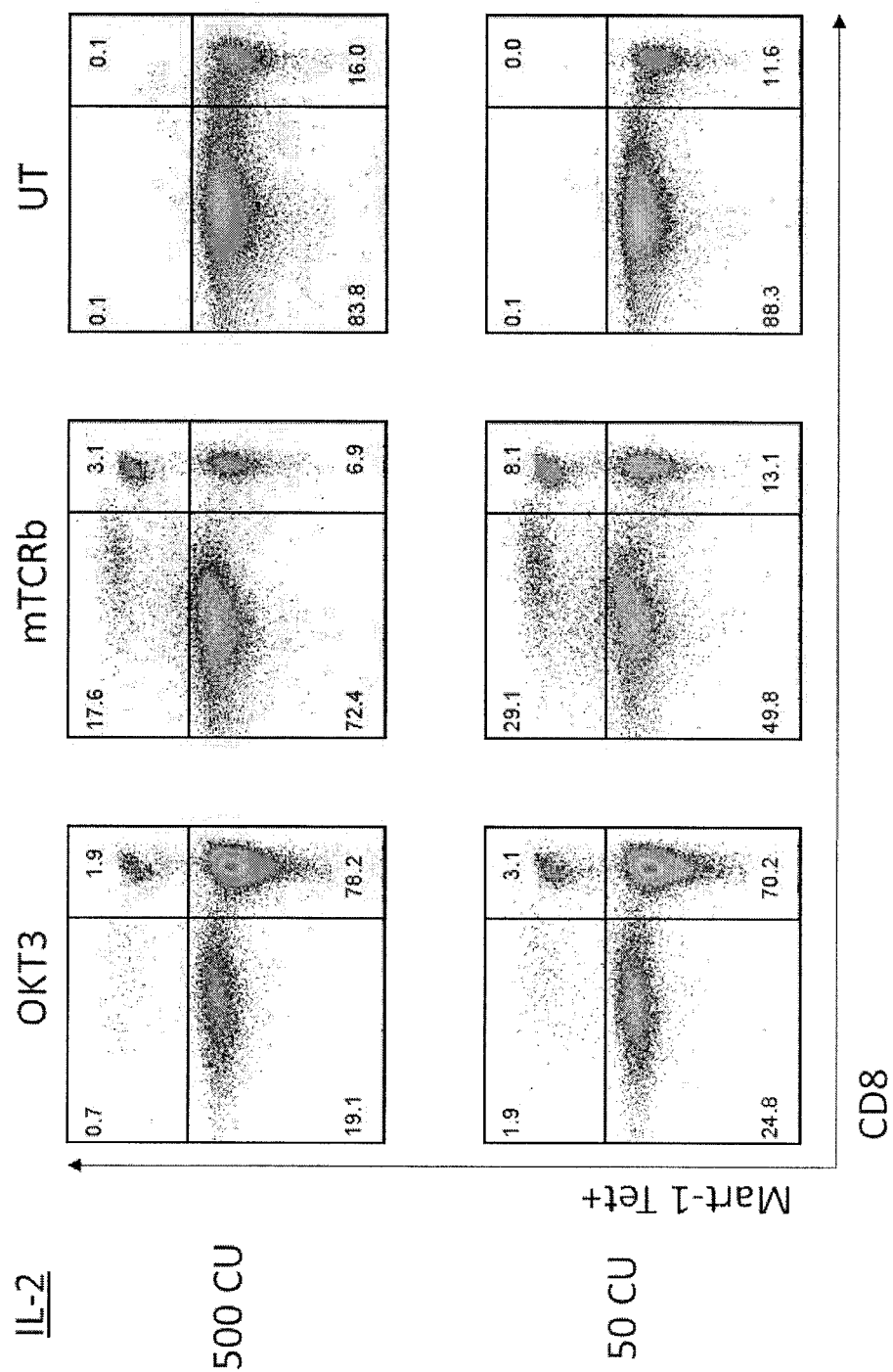

FIG. 9 shows experimental data (dot plots) illustrating CD8 expression and anti-MART-1 TCR expression detected by FACS for UT cells or the diluted transduced cells of FIG. 8C following expansion with (i) 50 CU or 500 CU of IL-2 and (ii) OKT3 Ab or H57 Ab ("mTCRb").

Figure 10B:
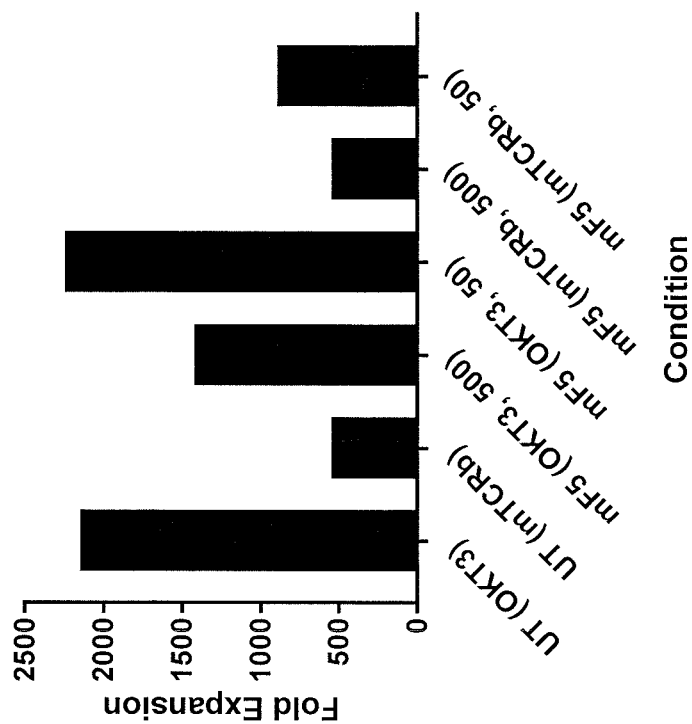
Figure 10A:
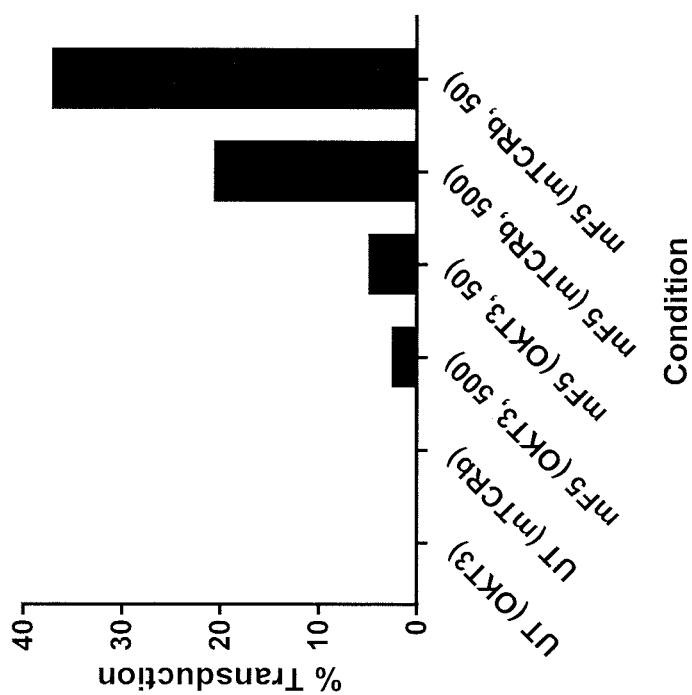

FIG. 10A is a graph showing the percentage of transduced cells detected for UT cells or the diluted transduced cells of FIG. 8C following expansion with (i) 50 CU or 500 CU of IL-2 and (ii) OKT3 Ab or H57 Ab ("mTCRb").

FIG. 10B is a graph showing the fold expansion achieved for UT cells or the diluted transduced cells of FIG. 8C following expansion with (i) 50 CU or 500 CU of IL-2 and (ii) OKT3 Ab or H57 Ab ("mTCRb").

Figures 11A, 11B, 11C:
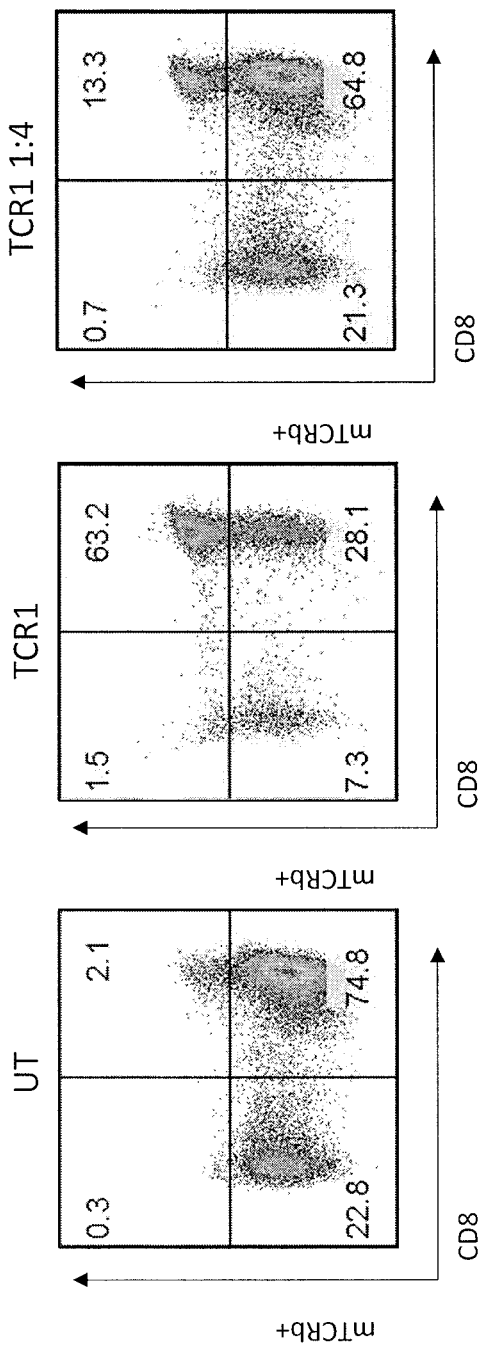

FIGS. 11A-11C show experimental data (dot plots) illustrating CD8 expression and mTCRb expression detected by FACS prior to expansion of UT cells (FIG. 11A) or cells transduced with an anti-MART-1 TCR before (FIG. 11B) and after (FIG. 11C) a four-fold dilution.

FIGS. 12A-12E show experimental data (dot plots) illustrating CD8 expression and mTCRb expression detected by FACS following expansion of UT cells (FIG. 12E) or the diluted TCR-transduced cells of FIG. 11C with OKT3 and 500 CU IL-2 (FIG. 12A), H57 (mTCRb) and 500 CU IL-2 (FIG. 12B), H57 (mTCRb) and 50 CU IL-2 (FIG. 12C), or H57 (mTCRb) and no IL-2 (FIG. 12D).

Figures 13A, 13B:
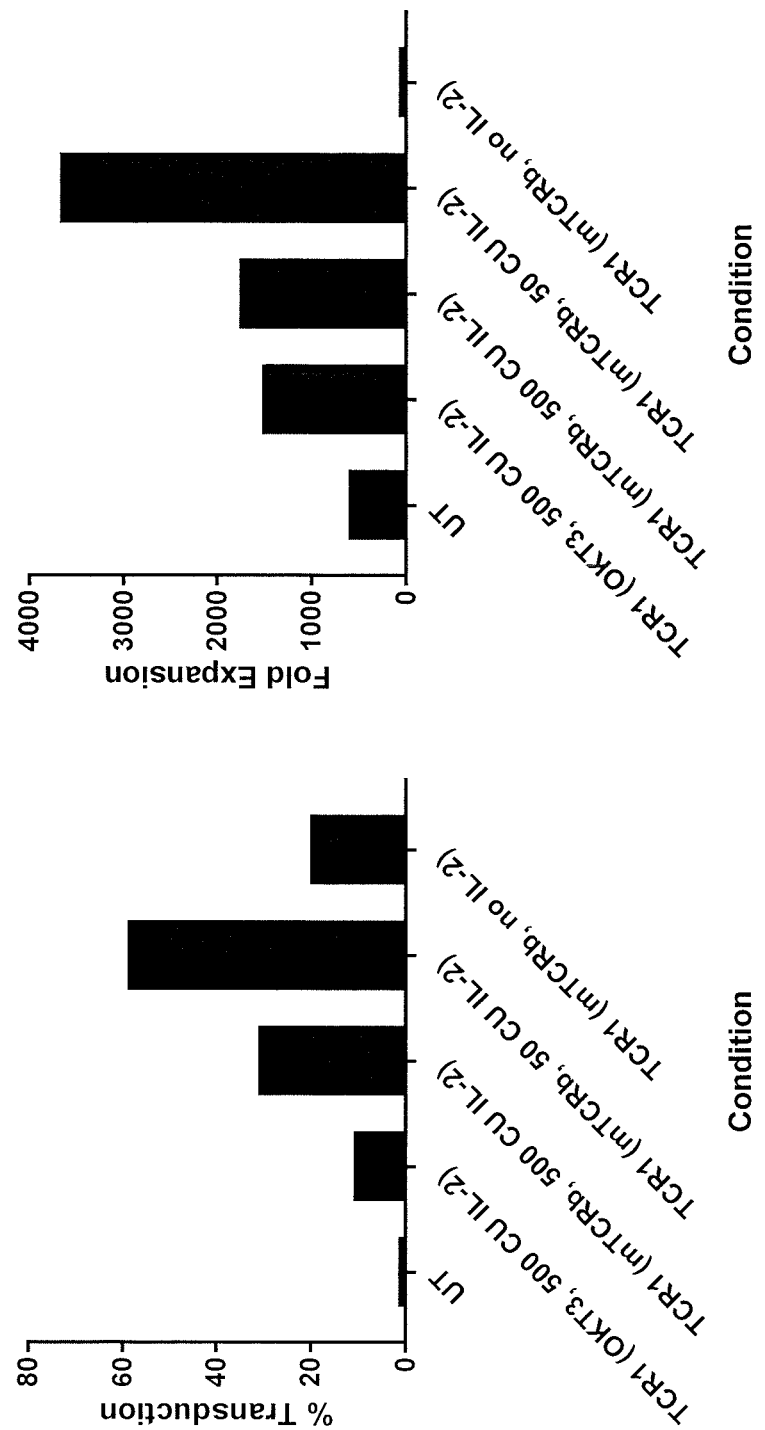

FIG. 13A is a graph showing the percentage of transduced cells detected for UT cells or the diluted transduced cells of FIG. 11C following expansion with (i) 0 CU, 50 CU or 500 CU of IL-2 and (ii) OKT3 Ab or H57 Ab ("mTCRb").

FIG. 13B is a graph showing the fold expansion achieved for UT cells or the diluted transduced cells of FIG. 11C following expansion with (i) 0 CU, 50 CU or 500 CU of IL-2 and (ii) OKT3 Ab or H57 Ab ("mTCRb").

FIGS. 14A-14F show experimental data (dot plots) illustrating CD8 expression and mTCRb expression detected by FACS prior to expansion (FIG. 14A) or following expansion of transduced cells with OKT3 (30 ng/ml) (FIG. 14B) or H57 (mTCRb) (5 ng/ml (FIG. 14F), 10 ng/ml (FIG. 14E), 50 ng/ml (FIG. 14D), or 500 ng/ml (FIG. 14C)).

Figure 15:
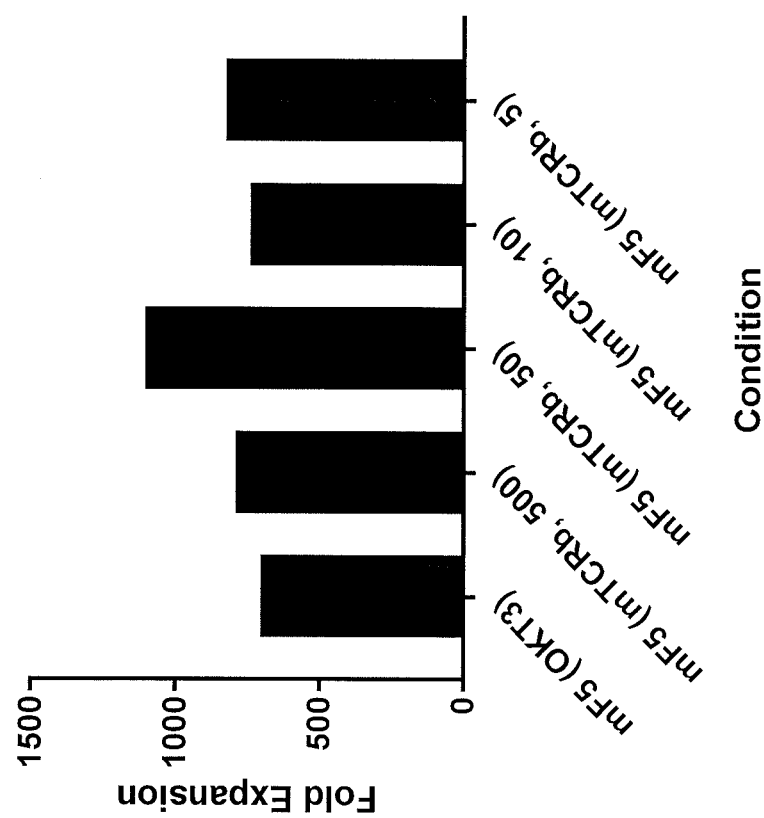

FIG. 15 is a graph showing the fold expansion achieved for mTCR-transduced cells following expansion with OKT3 (30 ng/ml) or H57 (mTCRb) (5, 10, 50, or 500 ng/ml).

FIGS. 16A-16E show experimental data (dot plots) illustrating CD8 expression and mTCRb expression detected by FACS following a second round of expansion of mTCR-transduced cells which underwent a first round of expansion with H57. The second round of expansion was carried out with OKT3 (30 ng/ml) (FIG. 16A) or H57 (mTCRb) (5 ng/ml (FIG. 16E), 10 ng/ml (FIG. 16D), 50 ng/ml (FIG. 16C), or 500 ng/ml (FIG. 16B)).

Figure 17:
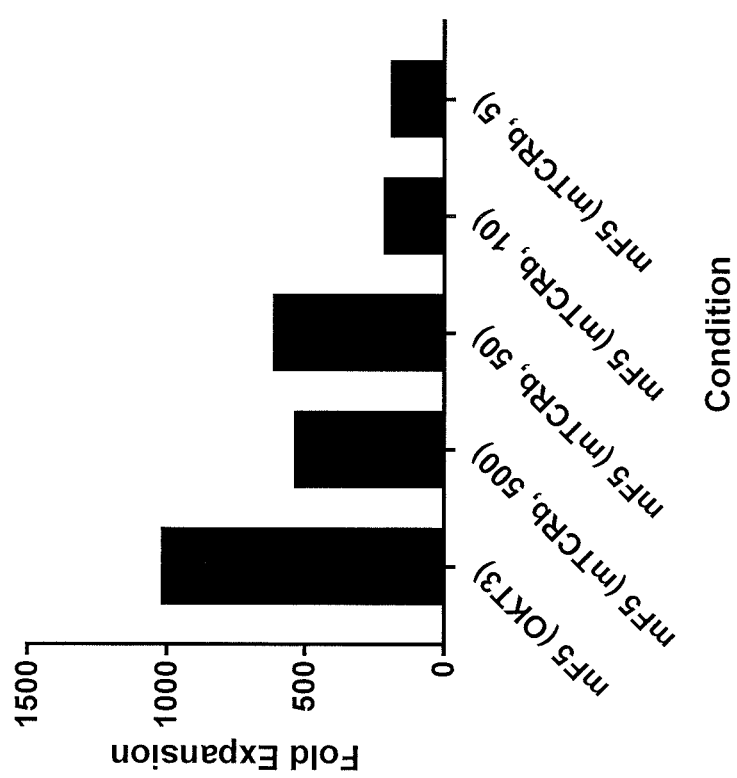

FIG. 17 graph showing the fold expansion achieved for mTCR-transduced cells following a second round of expansion of mTCR-transduced cells which underwent a first round of expansion with H57. The second round of expansion was carried out with OKT3 (30 ng/ml) or H57 (mTCRb) (5, 10, 50, or 500 ng/ml).

Figure 18:
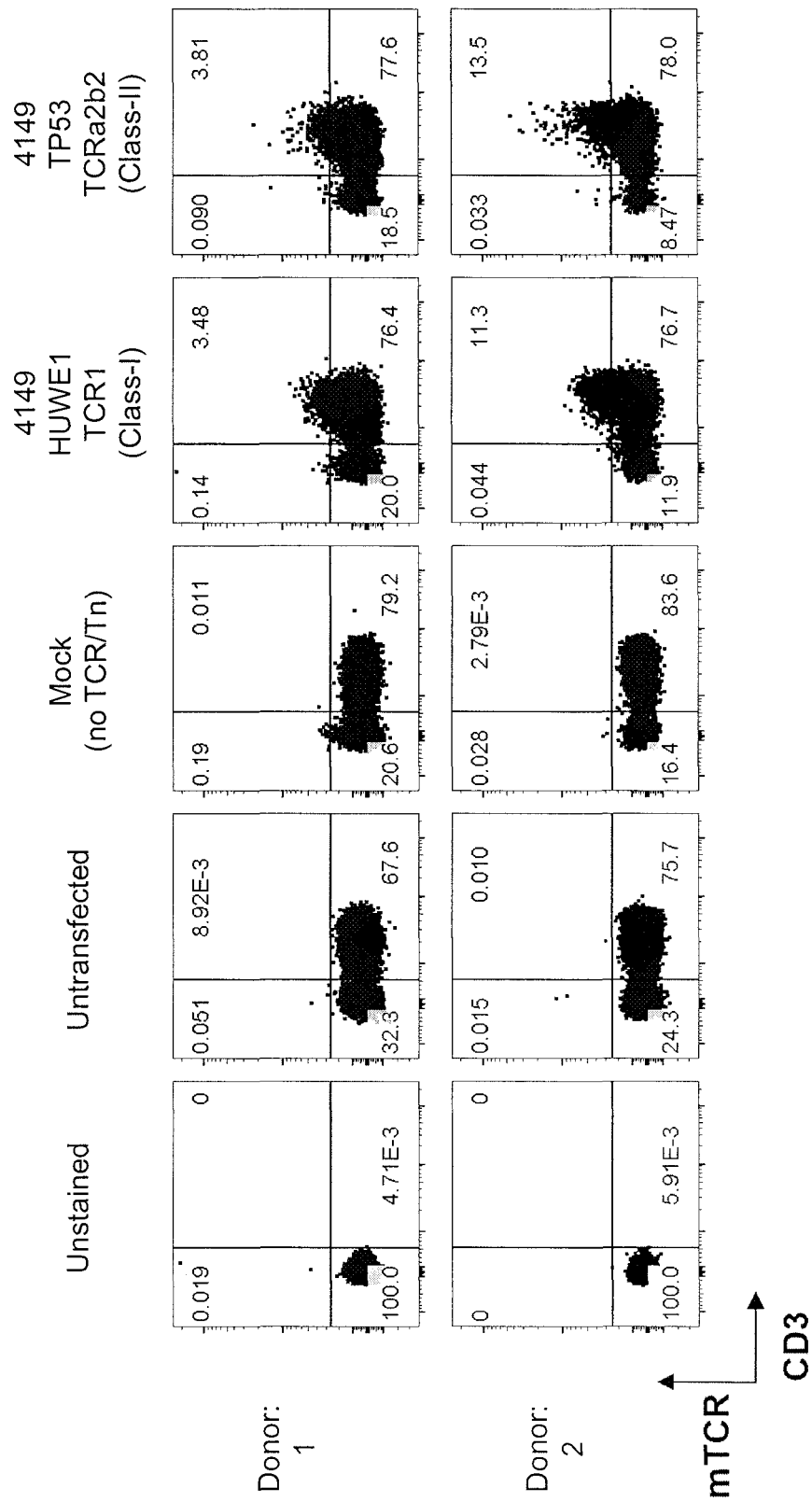

FIG. 18 shows experimental data (dot plots) illustrating CD3 expression and mTCRb expression detected by FACS the day following electroporation of PBMC from Donors 1 and 2 with 4149-HUWE1-TCR1 or 4149-TP53-TCRa2b2. Unstained PBMC, untransfected PBMC, and PBMC electroporated with electroporation buffer only (Mock) (no TCR) served as negative controls.

Figures 19A, 19B:
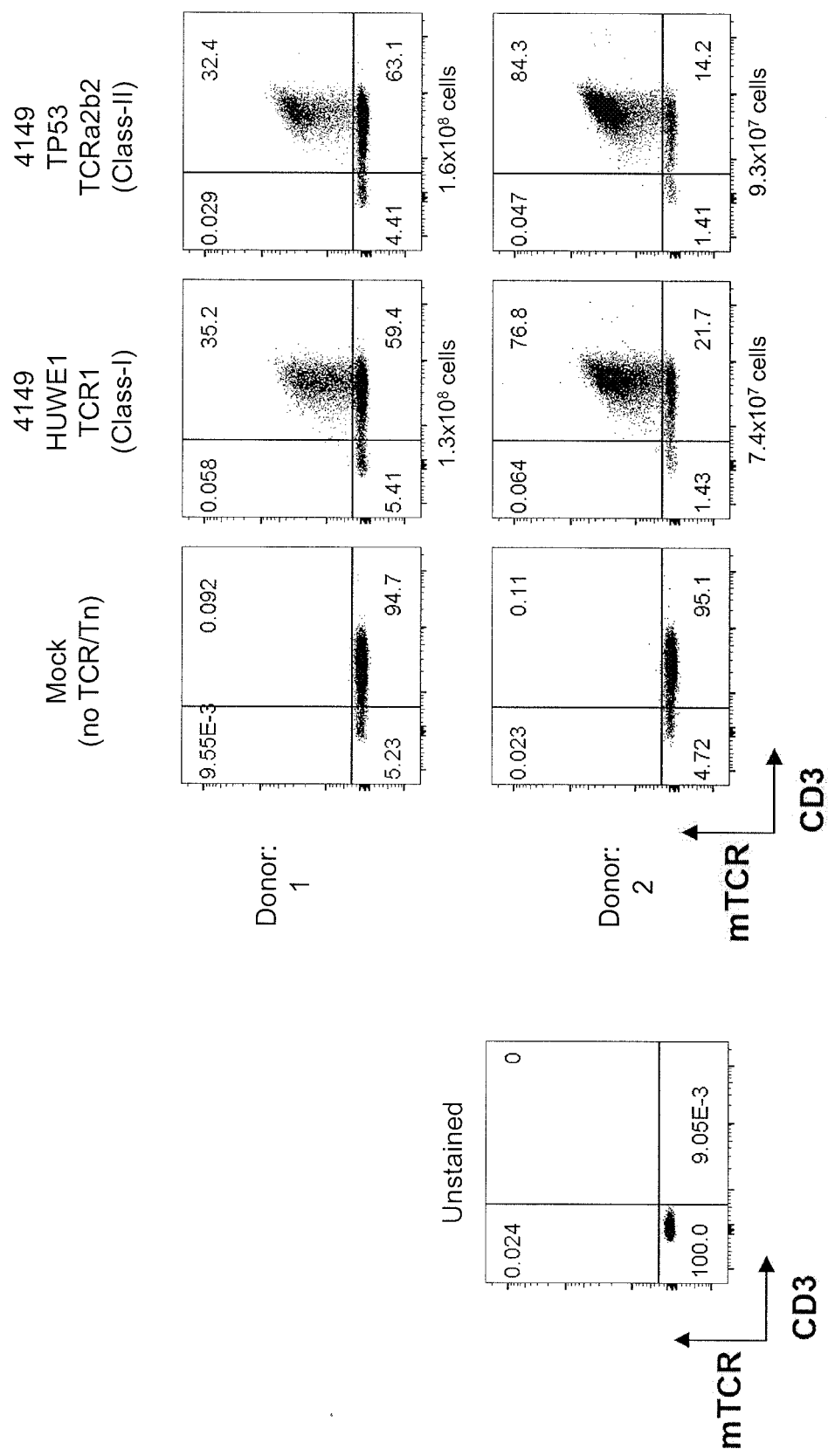

FIGS. 19A-19B show experimental data (dot plots) illustrating CD3 expression and mTCRb expression by PBMC from Donors 1 and 2 which were transposed with 4149-HUWE1-TCR1 or 4149-TP53-TCRa2b2 and which underwent one round of expansion with H57 (FIG. 19B). Unstained PBMC (FIG. 19A) and PBMC electroporated with electroporation buffer only (Mock) (no TCR) (FIG. 19B) served as negative controls.

Figures 20A, 20B:
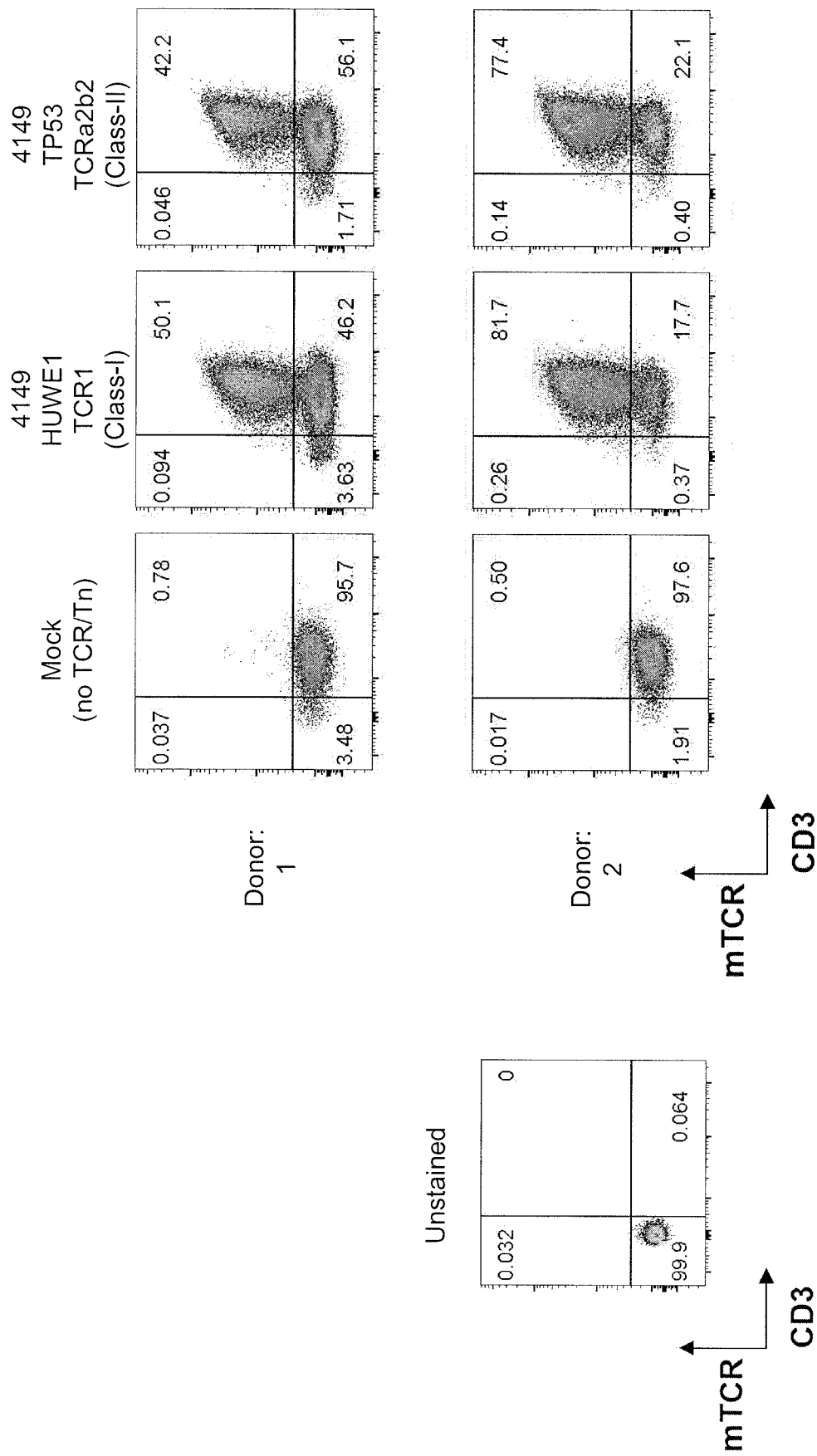

FIGS. 20A-20B show experimental data (dot plots) illustrating CD3 expression and mTCRb expression by PBMC from Donors 1 and 2 which were transposed with 4149-HUWE1-TCR1 or 4149-TP53-TCRa2b2 and which underwent one round of expansion with H57 (FIG. 20B) followed by expansion using the standard REP. Unstained PBMC (FIG. 20A) and PBMC electroporated with electroporation buffer only (Mock) (no TCR) (FIG. 20B) served as negative controls.

Figure 21A:
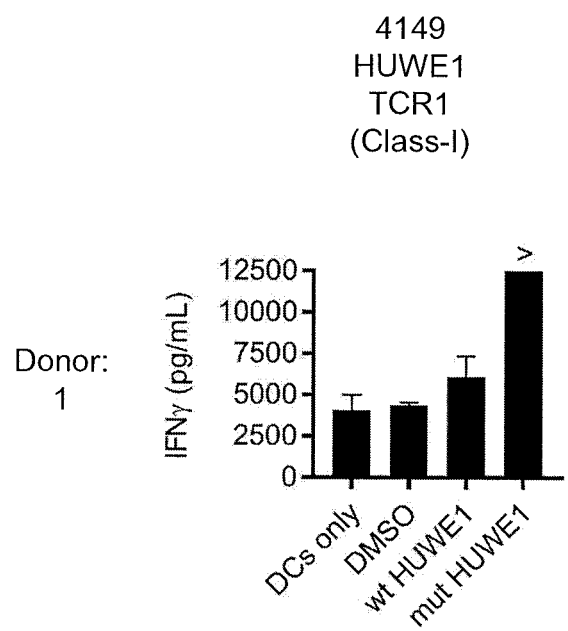

FIG. 21A is a graph showing the concentration of IFN-γ secreted following co-culture of (i) DCs pulsed with DMSO, WT HUWE1 peptide, or mutated (mut) HUWE1 peptide, with (ii) cells from Donor 1 transposed with 4149-HUWE1-TCR1. DCs cultured alone served as a control. Mean±SEM; n=3 technical replicates.

Figure 21B:
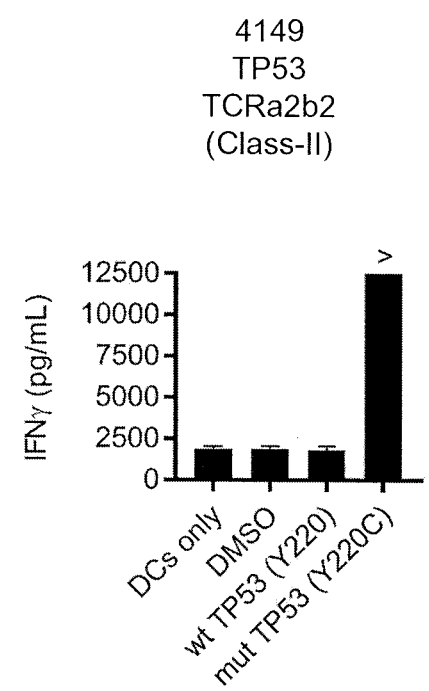

FIG. 21B is a graph showing the concentration of IFN-γ secreted following co-culture of (i) DCs pulsed with DMSO, WT TP53 peptide, or mut TP53 peptide with (ii) cells from Donor 1 transposed with 4149-TP53-TCRa2b2. DCs cultured alone served as a control. Mean±SEM; n=3 technical replicates.

Figure 21C:
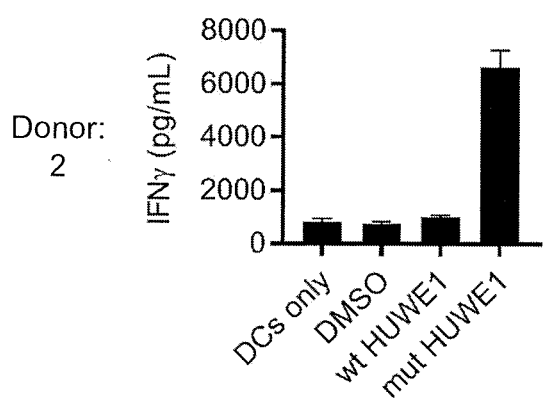

FIG. 21C is a graph showing the concentration of IFN-γ secreted following co-culture of (i) DCs pulsed with DMSO, WT HUWE1 peptide, mut HUWE1 peptide, with (ii) cells from Donor 2 transposed with 4149-HUWE1-TCR1. DCs cultured alone served as a control. Mean±SEM; n=3 technical replicates.

Figure 21D:
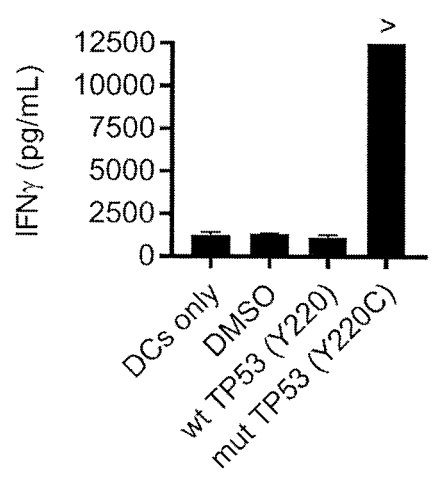

FIG. 21D is a graph showing the concentration of IFN-γ secreted following co-culture of (i) DCs pulsed with DMSO, WT TP53 peptide, or mut TP53 peptide with (ii) cells from Donor 2 transposed with 4149-TP53-TCRa2b2. DCs cultured alone served as a control. Mean±SEM; n=3 technical replicates.

Figure 22:
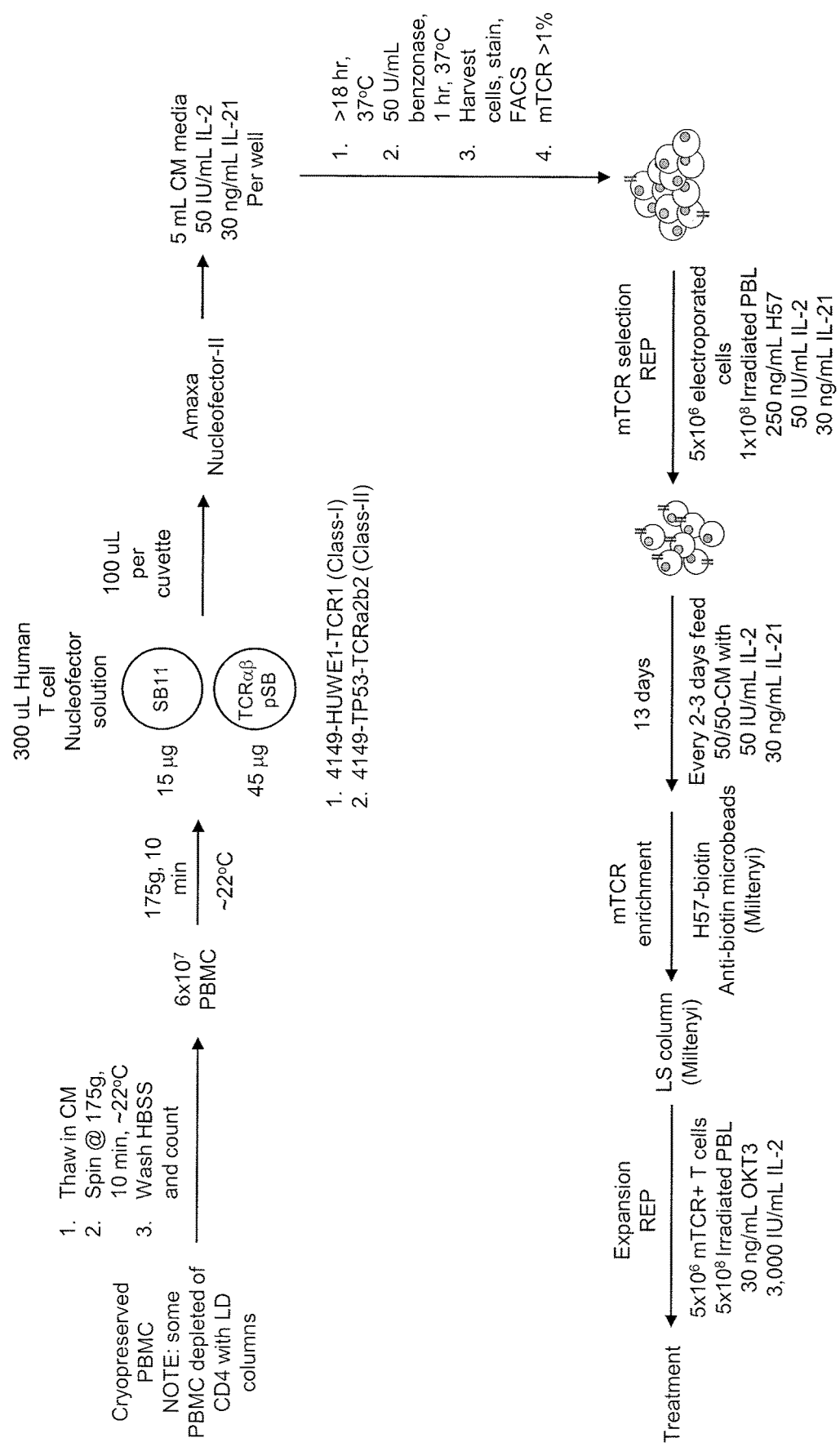

FIG. 22 is a schematic illustrating a method of selectively expanding the number of T cells expressing a TCR comprising a murine constant region (mTCR) in accordance with an embodiment of the invention.

FIG. 23A is a graph showing the total number cells in one cuvette measured at four time points during the method described in Example 14: following electroporation (open bars), following selective expansion with H57 (striped bars), following enrichment with H57-conjugated beads (grey bars), and following standard REP with OKT3 (black bars).

Cells were electroporated with 4149-HUWE1-TCR1 or 4149-TP53-TCRa2b2. Triplicate cuvettes were taken forward in parallel such that data shown are mean+/−SEM (n=3).

FIG. 23B is a graph showing the percentage of CD3+ mTCR+ cells in one cuvette measured at four time points during the method described in Example 14: following electroporation (open bars), following selective expansion with H57 (striped bars), following enrichment with H57-conjugated beads (grey bars), and following standard REP with OKT3 (black bars). Cells were electroporated with 4149-HUWE1-TCR1 or 4149-TP53-TCRa2b2. Triplicate cuvettes were taken forward in parallel such that data shown are mean+/−SEM (n=3).

FIGS. 23C-23D are graphs showing the percentage of 4149-HUWE1-TCR1-transposed (mTCR+) (FIG. 23C) or 4149-TP53-TCRa2b2-transposed (mTCR+) (FIG. 23D) cells measured at day 28 (post-OKT3 REP) of the method described in Example 14. PBMC electroporated with electroporation buffer only (Mock) (no TCR) served as a negative control. Mock is indicated by (1) and TCR-transposed cells are indicated by (2). Triplicate cuvettes were taken forward in parallel such that data shown are mean+/−SEM (n=3).

FIG. 23E is a graph showing the percentage of CD4+ mTCRβ+ cells (open bars) or CD8+mTCRβ+ cells (closed bars) measured at day 28 (post-OKT3 REP) of the method described in Example 14. The TCR was 4149-HUWE1-TCR1 or 4149-TP53-TCRa2b2. Triplicate cuvettes were taken forward in parallel such that data shown are mean+/−SEM (n=3).

Figure 24A:
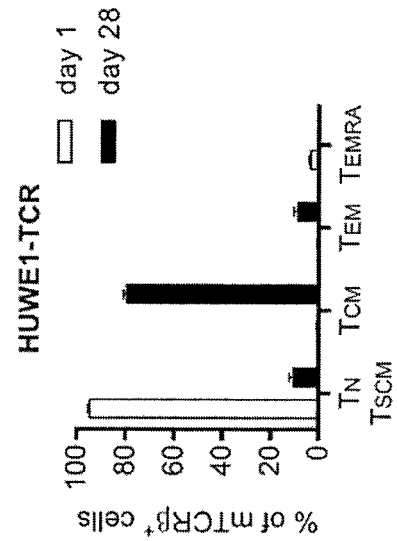

FIG. 24A is a graph showing the percentage of cells positive for the indicated markers measured before (Day 1) (open bars) or after (Day 28) (closed bars) expansion of the numbers of cells. The cells were transposed with the 4149-HUWE1-TCR1.

Figure 24B:
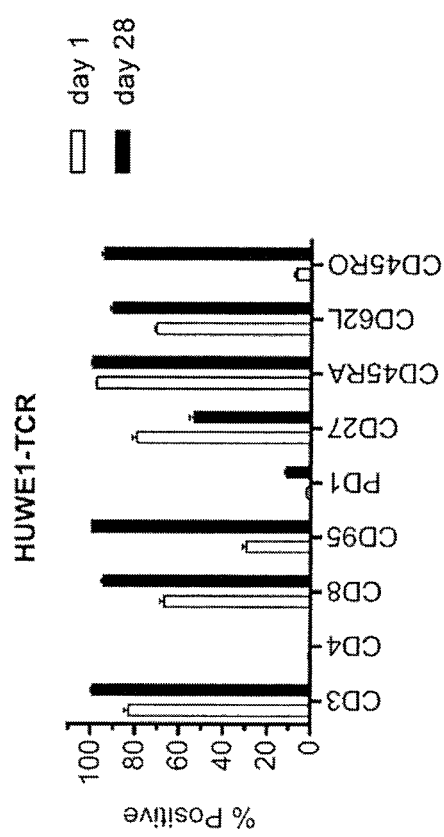

FIG. 24B is a graph showing the percentage of mTCRβ+ cells with the indicated phenotypes measured before (Day 1) (open bars) or after (Day 28) (closed bars) expansion of the numbers of cells. The cells were transposed with the 4149-HUWE1-TCR1. The phenotypes are central memory T ($T_{CM}$) cells, memory stem T cells ($T_{SCM}$ cells), naïve T cells ($T_N$), effector memory T cells ($T_{EM}$), and effector memory RA T cells ($T_{EMRA}$).

Figure 24C:
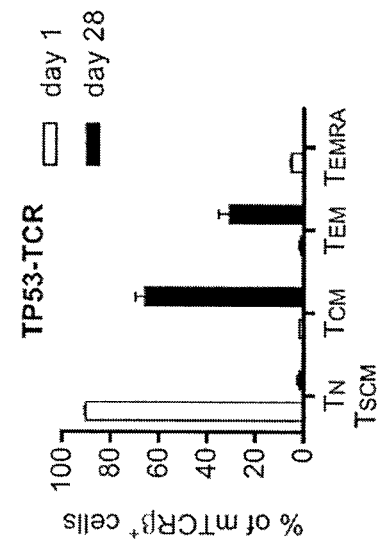

FIG. 24C is a graph showing the percentage of cells positive for the indicated markers measured before (Day 1) (open bars) or after (Day 28) (closed bars) expansion of the numbers of cells. The cells were transposed with the 4149-TP53-TCRa2b2.

Figure 24D:
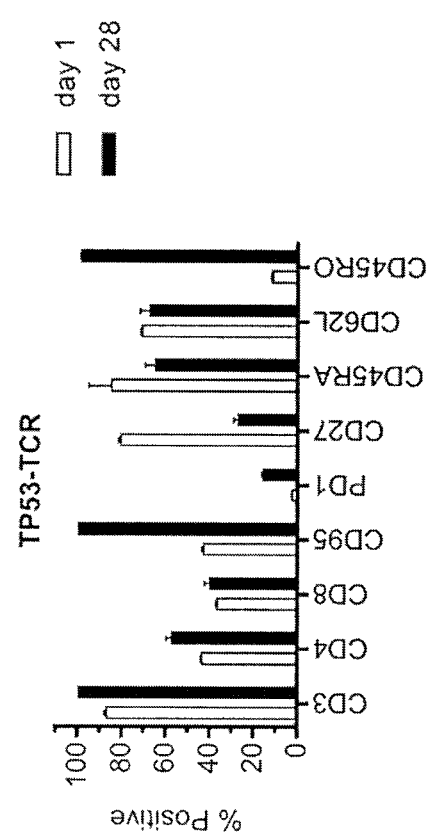

FIG. 24D is a graph showing the percentage of mTCRβ+ cells with the indicated phenotypes measured before (Day 1) (open bars) or after (Day 28) (closed bars) expansion of the numbers of cells. The cells were transposed with the 4149-TP53-TCRa2b2.

Figures 25A, 25B:
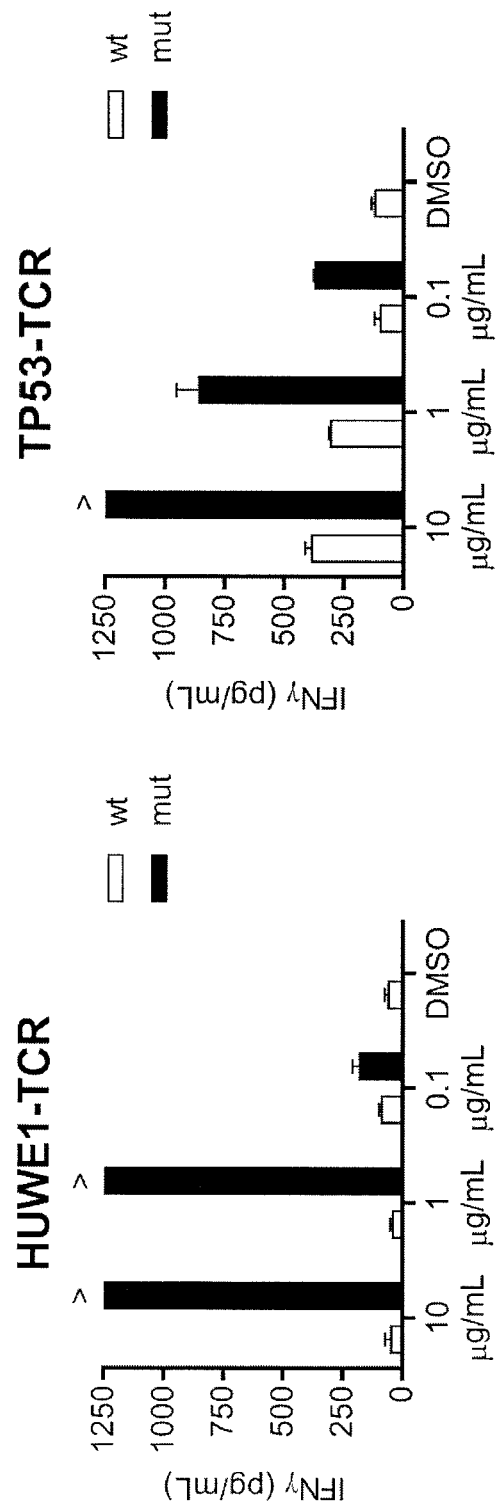

FIG. 25A is a graph showing the concentration of IFN-γ secreted following co-culture of (i) DCs pulsed with DMSO or 10, 1, or 0.1 µg/mL of WT HUWE1 peptide (open bars) or mut HUWE1 peptide (closed bars) with (ii) cells transposed with 4149-HUWE1-TCR1.

FIG. 25B is a graph showing the concentration of IFN-γ secreted following co-culture of (i) DCs pulsed with DMSO or 10, 1, or 0.1 µg/mL of WT TP53 peptide (open bars) or mut TP53 peptide (closed bars) with (ii) cells transposed with 4149-TP53-TCRa2b2.

DETAILED DESCRIPTION OF THE INVENTION

An embodiment of the invention provides a method of selectively expanding a number of T cells. The method may comprise modifying human T cells to express a TCR, wherein the TCR comprises a murine constant region (hereinafter, "mTCR"). The inventive methods may provide any one or more of a variety of advantages. For example, the inventive methods may provide for the selective expansion of the numbers of T cells expressing the mTCR over the number of cells which do not express the mTCR. The inventive methods may provide populations of cells with a larger proportion of cells which express the mTCR as compared to populations of cells prepared by methods which do not selectively expand the number of T cells as described herein. Without being bound to a particular theory or mechanism, it is believed that populations of cells with a larger proportion of cells which express the mTCR may provide one or both of improved destruction of target cancer cells and treatment of cancer as compared to populations of cells with a smaller proportion of cells which express the mTCR.

A TCR generally comprises two polypeptides (i.e., polypeptide chains), such as an α-chain of a TCR, a β-chain of a TCR, a γ-chain of a TCR, a δ-chain of a TCR, or a combination thereof. Such polypeptide chains of TCRs are known in the art. The mTCR can comprise any amino acid sequence, provided that the mTCR comprises a murine constant region and can specifically bind to and immunologically recognize an antigen, such as a condition-associated antigen or epitope thereof.

The mTCR may be an exogenous TCR, i.e., a TCR that is not native to (not naturally-occurring on) the T cell. An exogenous TCR may be a recombinant TCR. A recombinant TCR is a TCR which has been generated through recombinant expression of one or more exogenous TCR α-, β-, γ-, and/or δ-chain encoding genes. Methods of making recombinant TCRs are known in the art.

In an embodiment of the invention, the mTCR comprises two polypeptide chains, each of which comprises a variable region comprising a complementarity determining region (CDR) 1, a CDR2, and a CDR3 of a TCR. Preferably, the mTCR comprises the CDR1 of an α chain, the CDR2 of an α chain, the CDR3 of an α chain, the CDR1 of a β chain, the CDR2 of a β chain, and the CDR3 of a β chain.

In an embodiment, the mTCR can comprise an amino acid sequence of a variable region of a TCR comprising the CDRs set forth above. In this regard, the TCR may comprise an α chain variable region and a β chain variable region.

In an embodiment of the invention, the mTCR further comprises a murine constant region in addition to the variable region or CDRs described above. Preferably, the mTCR comprises both an α chain murine constant region and a β chain murine constant region. As used herein, the term "murine," when referring to a TCR or any component of a TCR described herein (e.g., complementarity determining region (CDR), variable region, constant region, alpha chain, and/or beta chain), means a TCR (or component thereof) which is derived from a mouse, i.e., a TCR (or component thereof) that originated from or was, at one time, expressed by a mouse T cell.

The mTCR may comprise a TCR α chain comprising a variable region and a constant region and a TCR β chain comprising a variable region and a constant region. The α chain variable region and the β chain variable region are hereinafter collectively referred to as the "variable region" of the TCR. The α chain constant region and the β chain constant region are hereinafter collectively referred to as the "constant region" of the TCR.

In an embodiment of the invention, the mTCR is a murine TCR. A murine TCR may comprise polypeptide chains derived entirely from a mouse. In this regard, the murine TCR may comprise a murine variable region and a murine constant region. Examples of murine TCRs include, but are not limited to, those disclosed in U.S. Pat. Nos. 8,216,565 and 9,487,573 and U.S. patent application Ser. No. 15/528,813.

In another embodiment of the invention, the mTCR is a chimeric or hybrid TCR comprised of amino acid sequences derived from TCRs from two different mammalian species, namely, a mouse and a non-mouse species. For example, the mTCR can comprise a human variable region and a murine constant region. Examples of chimeric TCRs comprising a human variable region and a mouse constant region are disclosed in Patent Application Nos. PCT/US2016/050875, PCT/US2017/044615, PCT/US2017/027865, U.S. Patent Application Publication Nos. 2013/0274203, 2017/0145070, and 2016/0152681; and U.S. Pat. No. 8,785,601.

In an embodiment of the invention, the mTCR is an antigen-specific TCR. The phrases "antigen-specific" and "antigenic specificity," as used herein, mean that the mTCR can specifically bind to and immunologically recognize an antigen, or an epitope thereof, such that binding of the mTCR to antigen, or the epitope thereof, elicits an immune response.

The antigen which is recognized by the antigen-specific mTCR can be any antigen which is characteristic of a condition. For example, the antigen may be, but is not limited to, a cancer antigen (also termed a tumor antigen or a tumor associated antigen) or a viral antigen. Viral antigens are known in the art and include, for example, any viral protein, e.g., env, gag, pol, gp120, thymidine kinase, and the like.

The term "cancer antigen," as used herein, refers to any molecule (e.g., protein, polypeptide, peptide, lipid, carbohydrate, etc.) solely or predominantly expressed or overexpressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host. Cancer antigens are known in the art and include, for instance, mesothelin, CD19, CD22, CD276 (B7H3), gp100, MART-1, Epidermal Growth Factor Receptor Variant III (EGFRVIII), TRP-1, TRP-2, tyrosinase, mutated KRAS, NY-ESO-1 (also known as CAG-3), MAGE-1, MAGE-3, etc.

In an embodiment, the cancer antigen is a neoantigen. A neoantigen is tumor-specific or cancer-specific antigen generated from gene mutations occurring in tumor cells or cancer cells during neoplastic transformation. A neoantigen may be unique to the patient. In a preferred embodiment, the neoantigen is an immunogenic neoantigen.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells.

The condition which is associated with or is characterized by the antigen recognized by the antigen-specific mTCR can be any condition. For instance, the condition can be a cancer or a viral condition, as discussed herein.

The cancer may be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

For purposes herein, "viral condition" means a condition that can be transmitted from person to person or from organism to organism, and is caused by a virus. In an embodiment of the invention, the viral condition is caused by a virus selected from the group consisting of herpes viruses, pox viruses, hepadnaviruses, papilloma viruses, adenoviruses, coronoviruses, orthomyxoviruses, paramyxoviruses, flaviviruses, and caliciviruses. For example, the viral condition may be caused by a virus selected from the group consisting of respiratory syncytial virus (RSV), influenza virus, herpes simplex virus, Epstein-Barr virus, varicella virus, cytomegalovirus, hepatitis A virus, hepatitis B virus, hepatitis C virus, human immunodeficiency virus (HIV), human T-lymphotropic virus, calicivirus, adenovirus, and Arena virus.

The viral condition may be, for example, influenza, pneumonia, herpes, hepatitis, hepatitis A, hepatitis B, hepatitis C, chronic fatigue syndrome, sudden acute respiratory syndrome (SARS), gastroenteritis, enteritis, carditis, encephalitis, bronchiolitis, respiratory papillomatosis, meningitis, HIV/AIDS, and mononucleosis.

In an embodiment of the invention, the method comprises modifying human T cells to express the mTCR. The T cells may be isolated or purified. The term "isolated," as used herein, means having been removed from its natural environment. The term "purified," as used herein, means having been increased in purity, wherein "purity" is a relative term, and not to be necessarily construed as absolute purity. "Purified" T cells refers to T cells which have been separated from other natural components, such as tissues, cells, proteins, nucleic acids, etc.

The T cells can be any T cells, such as cultured T cells, e.g., primary T cells, or T cells from a cultured T cell line, e.g., Jurkat, SupT1, etc., or T cells obtained from a non-mouse mammal. If obtained from a non-mouse mammal, the T cells can be obtained from numerous sources, including but not limited to blood, bone marrow, lymph node, thymus, spleen, or other tissues or fluids. Cells can also be enriched for or purified. Preferably, the T cells are human T cells. The T cells can be any type of T cells and can be of any developmental stage, including but not limited to, CD4+/CD8+ double positive T cells, CD4+ helper T cells, e.g., $Th_1$ and $Th_2$ cells, CD4+ T cells, CD8+ T cells (e.g., cytotoxic T cells), peripheral blood mononuclear cells (PBMCs), peripheral blood leukocytes (PBLs), tumor infiltrating cells (TILs), memory T cells, naïve T cells, and the like.

The method may comprise modifying the human T cells to express the mTCR using any technique suitable for introducing the mTCR, or a nucleic acid encoding the mTCR, into the human T cells, and obtaining expression of the mTCR by the human T cells. Such techniques are described in, for example, Green and Sambrook, *Molecular Cloning: A Laboratory Manual,* $4^{th}$ ed., Cold Spring Harbor Press, Cold Spring Harbor, NY (2012). Examples of techniques which may be useful for modifying the human T cells to express the TCR include, but are not limited to, transfection, transformation, transduction, electroporation, and gene editing techniques. In an embodiment of the invention, the human T cells are modified using transposons, lentiviral vectors, or retroviral vectors. Examples of transposons include, but are not limited to, SLEEPING BEAUTY transposon system (SBTS) (available from Intrexon (Germantown, MD) and Ziopharm (Boston, MA)), PIGGYBAC transposon system (available from Transposagen, Lexington, KY), and Tol2 transposon system. Examples of gene editing techniques may include the clustered regularly interspaced short palindromic repeats (CRISPR)/Cas system (Cheng et al., *Cell Res.,* 23: 1163-71 (2013)), meganucleases, zinc finger nucleases (ZFNs), and transcription activator-like effector-based nucleases (TALEN).

The method may further comprise producing a population of cells comprising a number of human T cells expressing the mTCR and a number of human T cells not expressing the mTCR. Modifying the human T cells to express the mTCR may be carried out with variable efficiency. Accordingly, the modifying of the human T cells to express the mTCR may result in a mixed population of cells including cells which express the mTCR as well as cells which do not express the mTCR.

The method may further comprise culturing the population of cells in the presence of (i) irradiated feeder cells, (ii) one or more cytokines, and (iii) an antibody, or an antigen-binding portion thereof, wherein the antibody specifically binds to the murine constant region of the mTCR, so as to selectively expand the number of T cells expressing the mTCR over the number of T cells not expressing the mTCR (also referred to herein as "selective expansion").

The irradiated feeder cells may comprise any irradiated feeder cells suitable for expanding the number of T cells. In an embodiment of the invention, the irradiated feeder cells comprise (i) irradiated allogeneic feeder cells; (ii) irradiated autologous feeder cells; or (ii) both (i) and (ii). The number of irradiated feeder cells employed is not limited and may be selected by the skilled artisan depending on a variety of factors such as, e.g., the application and the desired number of cells to be obtained. For example, multiples of $2 \times 10^7$ irradiated feeder cells may be useful for expansion in small-scale research studies. Multiples of $1 \times 10^8$ irradiated feeder cells may be useful for a medium-scale expansion. Multiples of about 2 to about 30 of $5 \times 10^8$ irradiated feeder cells may be useful for large-scale expansion (e.g., clinical production) (typically up to about $1.5 \times 10^{10}$). For example, the method may employ about $1 \times 10^9$ to about $4 \times 10^9$ allogeneic feeder cells and/or autologous feeder cells, preferably about $2 \times 10^9$ to about $3 \times 10^9$ allogeneic feeder cells and/or autologous feeder cells.

The one or more cytokines may comprise any one or more cytokines suitable for expanding the number of T cells. In an embodiment of the invention, the one or more cytokines comprise any one or more of interleukin (IL)-2, IL-7, IL-12, IL-15, and IL-21.

The method may further comprise culturing the population of cells in the presence of an antibody, or an antigen-binding portion thereof, wherein the antibody specifically binds to the murine constant region of the mTCR. The antibody can be any type of immunoglobulin that is known in the art. For instance, antibody may be a recombinant antibody. The antibody may be of any isotype, e.g., IgA, IgD, IgE, IgG (e.g., IgG1, IgG2, IgG3, or IgG4), IgM, etc. The antibody can be monoclonal or polyclonal. The antibody can be a naturally-occurring antibody, e.g., an antibody isolated and/or purified from a mammal, e.g., rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody, or antigen-binding fragment thereof, can have any level of affinity or avidity for the murine constant region of the mTCR.

In an embodiment of the invention, the antibody comprises two polypeptide chains (a heavy chain and a light chain), each of which comprises a variable region comprising a complementarity determining region (CDR) 1, a CDR2, and a CDR3 of an antibody. The antibody may comprise a heavy chain CDR1, a heavy chain CDR2, a heavy chain CDR3, a light chain CDR1, a light chain CDR2, and a light chain CDR3. In an embodiment of the invention, the antibody comprises a heavy chain variable region and a light chain variable region.

The antigen binding portion of the antibody can be any portion that has at least one antigen binding site. In an embodiment of the invention, the antigen binding portion may comprise the heavy chain CDR1, the heavy chain CDR2, the heavy chain CDR3, the light chain CDR1, the light chain CDR2, and the light chain CDR3 of the antibody. In another embodiment of the invention, the antigen binding portion may comprise the heavy chain variable region and the light chain variable region of the antibody. The antigen binding portion of the antibody may be a Fab fragment (Fab), F(ab')2 fragment, Fab' fragment, Fv fragment, single-chain variable region fragment (scFv), disulfide-stabilized variable region fragment (dsFv), scFv2CH3, scFv4, scFv3, scFv2, scFv-Fc, or a (scFv)2. A single-chain variable region fragment (scFv), which is a fusion protein including the variable (V) domain of an antibody heavy chain linked to a V domain of a light antibody chain via a synthetic peptide, can be generated using routine recombinant DNA technology techniques. Similarly, disulfide-stabilized variable region fragments (dsFv) can be prepared by recombinant DNA technology. The antigen binding portions of the antibody, however, are not limited to these exemplary types of antigen binding portions. Antibodies, and antigen binding portions thereof, are hereinafter collectively referred to as "antibodies" unless specified otherwise.

The antibody may be any antibody which specifically binds to the murine constant region of the mTCR. In an embodiment of the invention, the antibody specifically binds to the murine constant region of the mTCR and does not bind to any portion of a human TCR, e.g., a human TCR constant region or any portion of the human TCR complex.

The TCR complex comprises TCR α and β chains with three dimeric signaling chains: CD3δ/ε, CD3γ/ε and CD247ζ/ζ or ζ/η. The CD3δ/ε and CD3γ/ε chains are collectively referred to as the CD3 complex.

The antibody may specifically bind to the murine constant region of the α chain of the mTCR or the murine constant region of the β chain of the mTCR. In a preferred embodiment, the antibody specifically binds to the murine constant region of the β chain of the mTCR. The murine constant region of the mTCR β chain, to which the antibody specifically binds, may comprise or consist of the amino acid sequence of SEQ ID NO: 1 (the amino acid sequence of a full-length murine constant region of the mTCR β chain). The antibody may specifically bind to any portion of the murine constant region of the mTCR β chain. For example, the antibody may specifically bind to the amino acid sequence of SEQ ID NO: 2 (the amino acid sequence of an exemplary minimal epitope of the full-length murine constant region of the mTCR β chain). In an embodiment of the invention, the antibody specifically binds to amino acid residues D2, R4, N5, T7, E101, D103, K104, W105, P106, E107, G108, S109, and P110 of the amino acid sequence of SEQ ID NO: 1.

Antibodies which specifically bind to the murine constant region of the mTCR are commercially available. For example, an antibody which specifically binds to the murine constant region of the β chain of the mTCR is the H57 antibody (also referred to as H57-597) (available from Biolegend, San Diego, CA). H57 is an Armenian hamster IgG antibody and is described, for example, in Kubo et al., *J. Immunol.*, 142(8): 2736-42 (1989) and Grégoire et al., *PNAS*, 88: 8077-81 (1991). The epitope of the H57 antibody is described, for example, in Wang et al., *EMBO J.*, 17(1): 10-26 (1998). The H57 antibody specifically binds to amino acid residues D2, R4, N5, T7, E102, D104, K105, W106, P107, E108, G109, S110, and P111 of the amino acid sequence of SEQ ID NO: 1.

In an embodiment of the invention, the antibody comprises a heavy chain variable region and a light chain variable region. For example, the antibody (Ab) can comprise, consist of, or consist essentially of, the amino acid sequence of SEQ ID NO: 3 (the variable region of the H57 Ab heavy chain) or SEQ ID NO: 4 (the variable region of the H57 Ab light chain), or both SEQ ID NOs: 3 and 4. Preferably, the antibody comprises the amino acid sequences of both of SEQ ID NOs: 3 and 4. In an embodiment of the invention, the antibody comprises the complementarity determining region (CDR) 1, the CDR2, and the CDR3 of the H57 Ab heavy chain of SEQ ID NO: 3 and the CDR1, the CDR2, and the CDR3 of the H57 Ab light chain of SEQ ID NO: 4.

In an embodiment of the invention, the antibody comprises a heavy chain and a light chain comprising the variable regions set forth above. For example, the antibody can comprise, consist of, or consist essentially of, the amino acid sequence of SEQ ID NO: 5 (the H57 Ab heavy chain) or SEQ ID NO: 6 (the H57 Ab light chain), or both SEQ ID NOs: 5 and 6. Preferably, the antibody comprises the amino acid sequences of both of SEQ ID NOs: 5 and 6.

Culturing the population of cells in the presence of (i) irradiated feeder cells, (ii) one or more cytokines, and (iii) an antibody, as described herein, advantageously selectively expands the number of T cells expressing the mTCR over the number of T cells not expressing the mTCR. In this regard, the inventive methods may, advantageously, provide populations of cells with a larger proportion of cells which express the mTCR as compared to methods of expanding the number of cells which do not employ an antibody which specifically binds to the murine constant region of the TCR. In an embodiment of the invention, the method increases the number of T cells expressing the mTCR by about 5-fold or less to about 4,000-fold or more. For example, the inventive methods may increase the number of mTCR-expressing cells by about 5-fold to about 4,000-fold, about 100-fold to about 3,500-fold, about 1,000-fold to about 3,000-fold, about 1,500-fold to about 2,500-fold, about 10-fold to about 1,000-fold, about 50-fold to about 850-fold, about 100-fold to about 900-fold, about 150-fold to about 850-fold, about 200-fold to about 800-fold, about 250-fold to about 750-fold, about 300-fold to about 700-fold, about 350-fold to about 650-fold, or about 400-fold to about 600-fold. For example, the inventive methods may increase the number of mTCR-expressing cells by about 10-fold, about 50-fold, about 100-fold, about 150-fold, about 200-fold, about 250-fold, about 300-fold, about 350-fold, about 400-fold, about 450-fold, about 500-fold, about 550-fold, about 600-fold, about 650-fold, about 700-fold, about 750-fold, about 800-fold, about 850-fold, about 900-fold, about 950-fold, about 1,000-fold, or a range of any two of the foregoing values. The foregoing fold expansion may be achieved over a period of about 10 to about 14 days, preferably about 14 days. The fold expansion achieved by the inventive methods may be highly variable and may be donor-dependent.

In an embodiment of the invention, the method produces a selectively expanded population of cells, wherein about 10% to about 95% of the cells in the selectively expanded population express the TCR comprising a murine constant region. In this regard, the method may produce a selectively expanded population of cells, wherein about 10% to about 95%, about 15% to about 90%, about 20% to about 85%, about 25% to about 80%, about 30% to about 75%, about 35% to about 70%, or about 40% to about 65% of the cells in the selectively expanded population express the mTCR. The method may produce a selectively expanded population of cells, wherein about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or a range of any two of the foregoing values, of the cells in the selectively expanded population express the mTCR.

The inventive methods may, advantageously produce any number of mTCR-expressing T cells which may be suitable for any of a variety of applications. In an embodiment of the invention, the method may produce about $1\times10^6$ to about $1\times10^{11}$ or more T cells which express the mTCR. For example, in small vessels (e.g., a T25 flask), the inventive methods may produce about $1\times10^6$ to about $1\times10^7$ T cells which express the mTCR. In a larger vessel (e.g., a T175 flask), the inventive methods may produce about $5\times10^6$ to about $3\times10^7$ T cells which express the mTCR. In other vessels (e.g., a GREX flask, available from Wilson Wolf Manufacturing, New Brighton, MN), the inventive methods may produce about $1\times10^9$ to about $1\times10^{10}$ T cells which express the mTCR. A population of about $1\times10^6$ to about $1\times10^{10}$ T cells which express the mTCR may be useful for small-scale screening experiments. Larger number of cells which express the mTCR, e.g., about $1.5\times10^{10}$ or more may also be obtained using the inventive methods, e.g., for clinical applications. The number of mTCR-expressing T cells produced by the inventive methods may be highly variable and may be donor-dependent.

The method may comprise carrying out no more than a single round of selective expansion of the numbers of mTCR-expressing cells or multiple rounds of selective expansion of the numbers of mTCR-expressing cells. In an embodiment of the invention, the method comprises carrying out one or more rounds of selective expansion as described herein with respect to other aspects of the invention, followed by one or more rounds of non-selective expansion of the numbers of cells. In this regard, the method may further comprise culturing the human T cells in the presence of (i) one or both of irradiated allogeneic feeder cells and irradiated autologous feeder cells, (ii) one or more cytokines, and (iii) an antibody, or an antigen binding portion thereof, which specifically binds to the human CD3 complex (also referred to herein as "non-selective expansion"). Expansion of the numbers of T cells can be accomplished by any of a number of methods as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods*, 128:189-201 (1990). For example, the numbers of T cells can be non-selectively expanded using an antibody, or an antigen binding portion thereof, which specifically binds to the human CD3 complex in the presence of feeder lymphocytes and either interleukin-2 (IL-2) or interleukin-15 (IL-15), with IL-2 being preferred. An example of antibody which specifically binds to the human CD3 complex is OKT3 (available from Ortho-McNeil, Raritan, N.J.).

Multiple rounds of selective expansion, or one or more rounds of selective expansion followed by one or more rounds of non-selective expansion, may increase the number of mTCR by about 100,000-fold or more. In an embodiment of the invention, the method produces a population of cells, wherein about 20% to about 99% of the cells in the population express the TCR comprising a murine constant region. Multiple rounds of selective expansion, or one or more rounds of selective expansion followed by one or more rounds of non-selective expansion, may produce a population of cells, wherein about 25% to about 95%, about 30% to about 90%, about 35% to about 85%, about 40% to about 80%, about 45% to about 75%, or about 50% to about 70% of the cells in the population express the mTCR. The method may produce a population of cells, wherein about 20%, about 25%, about 30%, about 35%, about 40%, about 45%, about 50%, about 55%, about 60%, about 65%, about 70%, about 75%, about 80%, about 85%, about 90%, about 95%, about 99%, or a range of any two of the foregoing values, of the cells in the population express the mTCR.

In an embodiment of the invention, the method further comprises separating the T cells which express the TCR from the T cells which do not express the TCR using the antibody, or an antigen-binding portion thereof, which specifically binds to the murine constant region of the TCR. In this regard, the method may comprise physically contacting a mixed population of cells comprising cells which express the mTCR and cells which do not express the mTCR with the antibody so that the antibody specifically binds to the murine constant region of the TCR. The antibody may be attached to a support, e.g., beads. The method may further comprise washing the antibody and the cells so that all or a portion of the cells which do not express the mTCR are removed from the cells that do express the mTCR. The method may further comprise eluting the mTCR-expressing cells from the antibody. Examples of techniques for separating T cells are described, for example, in Deniger et al., *Mol. Ther.*, 24(6):1078-89 (2016) and Field et al., *PLoS One*, 8(6):e68201 (2013).

The inventive methods may, advantageously provide a population of cells that is enriched for cells which express the mTCR. Accordingly, an embodiment of the invention provides a population of cells comprising a selectively expanded number of T cells prepared by any of the methods described herein. The population of cells can be a heterogeneous population comprising the mTCR-expressing cells together with at least one other cell, e.g., a T cell which does not express the mTCR, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of (e.g., consisting essentially of) mTCR-expressing T cells. The population also can be a clonal population of cells, in which all cells of the population are clones of a single T cell expressing the mTCR, such that all cells of the population express the mTCR. In one embodiment of the invention, the population of cells is a clonal population comprising T cells expressing the mTCR.

The inventive populations of cells can be isolated and/or purified. The term "isolated," as used herein, means having been removed from its natural environment. The term "purified," as used herein, means having been increased in purity, wherein "purity" is a relative term, and not to be necessarily construed as absolute purity. For example, the purity can be at least about 50%, can be greater than about 60%, about 70%, about 80%, about 90%, about 95%, or can be about 100%.

The inventive populations of cells can be formulated into a composition, such as a pharmaceutical composition. In this regard, the invention provides a pharmaceutical composition comprising any of the populations of cells described herein and a pharmaceutically acceptable carrier. The inventive pharmaceutical compositions may comprise any of the inventive populations of cells in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for T cells. Methods for preparing administrable compositions are known or apparent to those skilled in the art and are described in more detail in, for example, *Remington: The Science and Practice of Pharmacy*, 22$^{nd}$ Ed., Pharmaceutical Press (2012). It is preferred that the pharmaceutically acceptable carrier be one which has no detrimental side effects or toxicity under the conditions of use.

The choice of carrier may be determined by the particular method used to administer the inventive population of cells. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the inventive populations of cells, and in certain instances, a particular route can provide a more immediate and more effective response than another route.

Preferably, the inventive population of cells is administered by injection, e.g., intravenously. The pharmaceutically acceptable carrier for cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA- LYTE A (Baxter, Deerfield, IL), about 5% dextrose in water, or Ringer's lactate. In an embodiment, the pharmaceutically acceptable carrier is supplemented with human serum albumen. A pharmaceutical composition for infusion may or may not contain IL-2. If the pharmaceutical composition contains IL-2, then a concentration of about 300 IU/mL can be used.

For purposes of the invention, the amount or dose (e.g., numbers of cells) administered should be sufficient to effect, e.g., a therapeutic or prophylactic response, in the mammal over a reasonable time frame. For example, the dose (e.g., numbers of cells) should be sufficient to bind to a condition-associated antigen, or detect, treat or prevent a condition in a period of from about 2 hours or longer, e.g., 12 to 24 or more hours, from the time of administration. In certain embodiments, the time period could be even longer. The dose will be determined by the efficacy of the population of cells and the condition of the mammal (e.g., human), as well as the body weight of the mammal (e.g., human) to be treated.

Many assays for determining an administered dose are known in the art. For purposes of the invention, an assay, which comprises comparing the extent to which target cells are lysed or IFN-γ is secreted by T cells expressing the mTCR upon administration of a given dose of such T cells to a mammal among a set of mammals of which each is given a different dose of the T cells, could be used to determine a starting dose to be administered to a mammal. The extent to which target cells are lysed or IFN-γ is secreted upon administration of a certain dose can be assayed by methods known in the art.

The dose of the inventive population of cells also will be determined by the existence, nature and extent of any adverse side effects that might accompany the administration of a particular population of cells. Typically, the attending physician will decide the dosage of the population of cells with which to treat each individual patient, taking into consideration a variety of factors, such as age, body weight, general health, diet, sex, inventive population of cells to be administered, route of administration, and the severity of the condition being treated. In an embodiment, the number of cells administered per infusion may vary, e.g., from about $1\times10^6$ to about $1\times10^{12}$ cells or more. In certain embodiments, at least about $1.5\times10^{10}$ cells may be administered.

The population of cells produced by the inventive methods may be useful for treating or preventing conditions, e.g., cancer. Accordingly, another embodiment of the invention provides a method of treating or preventing a condition in a mammal, the method comprising selectively expanding a number of T cells according to any of the methods described herein with respect to other aspects of the invention and administering the selectively expanded number of T cells to the mammal in an amount effective to treat or prevent the condition in the mammal.

For purposes of the inventive methods, wherein populations of cells are administered, the cells can be cells that are allogeneic or autologous to the mammal. Preferably, the cells are autologous to the mammal.

In an embodiment of the invention, the condition is cancer. The cancer may be any of the cancers described herein with respect to other aspects of the invention.

In an embodiment of the invention, the condition is a viral condition. The viral condition may be any of the viral conditions described herein with respect to other aspects of the invention.

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the condition, e.g., cancer, being treated or prevented. For example, the treatment or prevention provided by the inventive method can include promoting the regression of a tumor. Also, for purposes herein, "prevention" can encompass delaying the onset of the condition, or a symptom or condition thereof.

The following examples further illustrate the invention but, of course, should not be construed as in any way limiting its scope.

EXAMPLE 1

This example demonstrates that selectively expanding the number of T cells which express a TCR including a murine constant region (mTCR) increases the number of cells which express the mTCR.

Figure 1A:
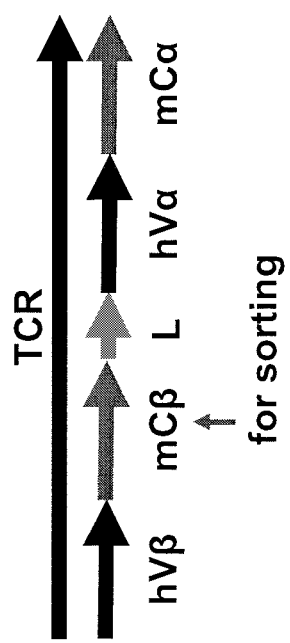
FIG. 1A is a schematic illustrating a nucleotide construct encoding a human TCR α chain variable region (hVα), a murine TCR α chain constant region (mCα), a synthetic linker sequence (L), a human TCR β chain variable region (hVβ), and a murine TCR β chain constant region (mCβ).

RNA encoding two TCRs, one having antigenic specificity for the cancer-specific, mutated ERBB2 neoantigen, and the other having antigenic specificity for the cancer specific, mutated ERBB2IP neoantigen were isolated from tumor infiltrating lymphocytes (TIL) isolated from a cancer patient. cDNA was amplified from the RNA through reverse transcription, followed by PCR amplification of the cDNA copies. mTCR constructs (one for each TCR) were prepared as described in Deniger et al., *Mol. Ther.*, 24(6):1078-89 (2016). Briefly, the human TCR-α-V-J regions were fused to the mouse TCR-α constant chain, and the human TCR-β-V-D-J regions were fused to the mouse TCR-β constant chains, with a synthetic linker sequence positioned between the alpha (α) and beta (β) chains (FIG. 1A). Both mTCR constructs were synthesized and cloned into SLEEPING BEAUTY Transposon System (SBTS)) plasmids (available from Intrexon (Germantown, MD) and Ziopharm (Boston, MA)) and described in Deniger et al., *PLoS One*, 10(6): e0128151 (2015) and Singh et al., *Cancer Res.*, 71(10): 3516-27 (2011).

Figure 1B:
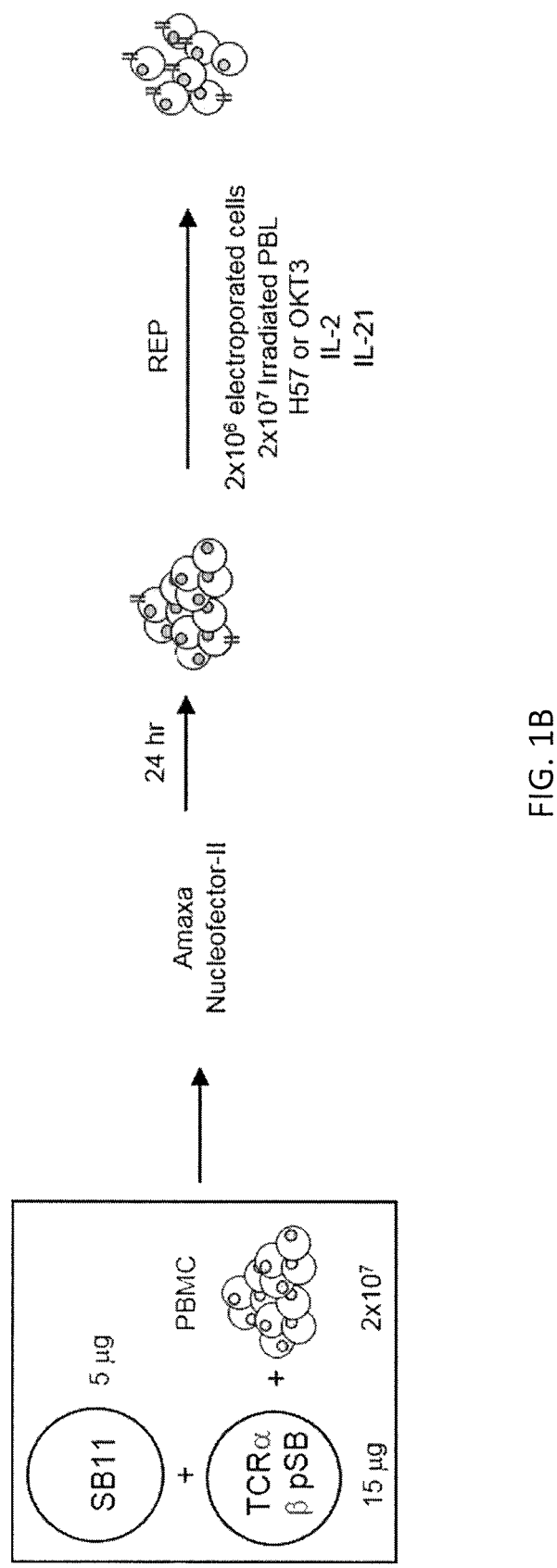
FIG. 1B is a schematic illustrating a method of selectively expanding the number of T cells expressing the mTCR in accordance with an embodiment of the invention.

A schematic illustrating a method of electroporating peripheral blood mononuclear cells (PBMC) with an mTCR and selectively expanding the number of mTCR$^+$ T cells in accordance with an embodiment of the invention is shown in FIG. 1B. As shown in FIG. 1B, a SBTS plasmid encoding one of each of the two mTCRs (15 μg) and a SBTS plasmid encoding transposase (5 μg) were respectively electroporated into autologous PBMC ($2\times10^7$) using an AMAXA NUCLEOFECTOR II device and kit (Lonza, Basel, Switzerland). After 24 hours, a mixed population of electroporated cells comprising cells which expressed the mTCR and cells which did not express the mTCR was obtained.

As shown in FIG. 1B, the number of T cells expressing the murine TCR constant region (mTCR$^+$ T cells) in the mixed population was selectively expanded. To selectively expand the mTCR$^+$ T cells, cells from the mixed population of electroporated cells ($2\times10^6$) were co-cultured with irradiated peripheral blood lymphocytes (PBL) ($2\times10^7$) in the presence of (i) H57 antibody (Ab) (Biolegend, San Diego, CA) or OKT3 antibody, (ii) IL-2, and (iii) IL-21.

Following selective expansion of the number of mTCR$^+$ T cells, the cells were stained with (i) anti-CD3 Ab, anti-CD4 Ab, or anti-CD8 Ab and (ii) anti-mTCRβ antibody (H57). PBMC electroporated with electroporation buffer only (Mock) (no TCR) served as a negative control.

The stained cells were counted by fluorescence activated cell sorting (FACS). The results are shown in FIG. 2. As shown in FIG. 2, selective expansion with the H57 Ab increased the number of anti-mutated ERBB2 mTCR$^+$ T cells and the number of anti-mutated ERBB2IP mTCR$^+$ T cells compared to OKT3.

EXAMPLE 2

This example demonstrates that a higher number of mTCR$^+$ is obtained with higher concentrations of H57 Ab.

PBMC were electroporated with the anti-ERBB2IP mTCR or the anti-ERBB2 mTCR construct as described in Example 1. The number of T cells expressing the murine TCR constant region (mTCR$^+$ T cells) in the mixed population were selectively expanded as described in Example 1 with various concentrations of H57 Ab (0 ng/mL, 1 ng/mL, 5 ng/mL, 10 ng/mL, 25 ng/mL, 50 ng/mL, 100 ng/mL, 250 ng/mL, or 500 ng/mL).

Following selective expansion of the number of mTCR$^+$ T cells, the cells were stained with (i) anti-CD3 Ab, anti-CD4 Ab, or anti-CD8 Ab and (ii) anti-mTCRβ antibody (H57). PBMC electroporated with electroporation buffer only (Mock) (no TCR) served as a negative control. Electroporated cells which underwent standard REP with OKT3 Ab (30 ng/mL) instead of selective expansion with H57 Ab served as a positive control for non-specific T cell growth.

The stained cells were counted by FACS. The results are shown in FIGS. 3A and 3B. As shown in FIGS. 3A and 3B, a higher number of anti-mutated ERBB2 mTCR$^+$ and anti-mutated ERBB2IP mTCR$^+$ cells was obtained with higher concentrations of H57 Ab.

EXAMPLE 3

This example demonstrates a method of selectively expanding the number of T cells which express a mTCR.

RNA encoding a TCR having antigenic specificity for a cancer-specific p53-Y220C neoantigen was isolated from tumor infiltrating lymphocytes isolated from ovarian cancer patient 4149. cDNA was amplified from the RNA through reverse transcription, followed by PCR amplification of the cDNA copies. mTCR constructs were prepared by fusing the human TCR-α-V-J regions to the mouse TCR-α constant chain, and the human TCR-β-V-D-J regions to the mouse TCR-β constant chains, with a synthetic linker sequence positioned between the α and β chains (FIG. 4B). mTCR constructs were synthesized and cloned into a SBTS plasmid.

A schematic illustrating a method of electroporating PBMC with the mTCR and selectively expanding the number of mTCR$^+$ T cells in accordance with an embodiment of the invention is shown in FIG. 4A. As shown in FIG. 4A, autologous PBMC were obtained from the patient and cryopreserved. Cryopreserved PBMC (200 g) were thawed at 20-23° C. for 10 minutes. The PBMC were placed in 50/50 media ($3\times10^6$ cells/mL) and cultured for 2 hours at 37° C. The SBTS plasmid encoding the mTCR and a SBTS plasmid encoding transposase were electroporated into the autologous PBMC using an AMAXA NUCLEOFECTOR II device and kit (Lonza, Basel, Switzerland). Human T cell NUCLEOFECTOR solution (300 μL) contained the SBTS plasmid encoding the mTCR (45 μg) and the SBTS plasmid encoding transposase (15 μg). This human T cell NUCLEOFECTOR solution was added to cuvettes (100 μL per cuvette). Electroporated cells were cultured in wells (5 mL 50/50 media/well) overnight at 37° C. After >18 hours, 50 U/mL benzonase was incubated at 37° C. for 1 hour. A mixed population of electroporated cells comprising cells which expressed the mTCR and cells which did not express the mTCR was obtained.

As shown in FIG. 4A, after over 18 hours of culture at 37° C., the number of T cells expressing the murine TCR constant region (mTCR$^+$ T cells) in the mixed population was selectively expanded. To selectively expand the mTCR$^+$ T cells, the mTCR$^+$ T cells ($5\times10^5$) were co-cultured with irradiated peripheral blood lymphocytes (PBL) ($1\times10^8$) in the presence of H57 Ab (Biolegend, San Diego, CA) (250 ng/mL), IL-2 (50 IU/mL), and IL-21 (30 ng/mL).

Following selective expansion of the number of mTCR$^+$ T cells, the number of mTCR$^+$ T cells was further expanded using the standard rapid expansion protocol (REP) (See Example 5). In the standard REP, the selectively expanded mTCR$^+$ T cells ($5\times10^6$) were co-cultured with irradiated PBL ($5\times10^8$), OKT3 antibody (30 ng/mL), and IL-2 (3000 IU/mL). The OKT3 antibody reacts with an epitope on the epsilon-subunit within the human CD3 complex.

COMPARATIVE EXAMPLE 1

This example demonstrates the number of electroporated cells which express the mTCR in the absence of selective expansion.

Autologous PBMC were electroporated with the SBTS plasmid encoding the mTCR and SBTS plasmid encoding transposase as described in Example 4. Negative controls included untransfected autologous PBMC and PBMC electroporated with electroporation buffer only (Mock). Electroporated cells were stained with anti-CD3 antibody and anti-mTCRβ antibody (H57). Unstained, untransfected autologous PBMC served as still another negative control.

On the day following electroporation, the stained cells were counted by FACS without undergoing selective expansion as described in Example 4. The FACS was gated on lymphocytes/PI$^{(neg)}$ cells. PI is a stain for dead cells. PI$^{(neg)}$ cells are live cells.

The results are shown in FIGS. 5A-5D. As shown in FIGS. 5A-5D, a modest number of the cells in the total population (about 5% of total cells) expressed the mTCR following electroporation without undergoing selective expansion.

EXAMPLE 4

This example demonstrates that selectively expanding electroporated T cells with the H57 antibody selectively increases the number of cells which express a TCR including a murine constant region in the mixed population.

Autologous PBMC were electroporated with the SBTS plasmid encoding the mTCR and SBTS plasmid encoding transposase, as described in Example 3. Various starting numbers of mTCR+ T cells ($1\times10^5$, $5\times10^5$, or $10\times10^5$) were selectively expanded as described in Example 3 using various concentrations of H57 Ab (250 ng/mL, 500 ng/mL, or 750 ng/mL). The experiment normalized input to $5\times10^5$ mTCR+ T cells based on the initial frequencies. For example, 5% mTCR expression meant that $1\times10^7$ total cells went into the expansion protocol to achieve $5\times10^5$ mTCR+ T cells. PBMC electroporated with electroporation buffer only (Mock) served as a negative control. The electroporated, selectively expanded cells were stained with anti-CD3 antibody and anti-mTCRβ antibody (H57).

The stained cells were counted by FACS. The FACS was gated on lymphocytes/PI$^{(neg)}$ cells. The results are shown in FIG. 6 and Tables 1-2. As shown in FIG. 6 and Tables 1-2, selective expansion with the H57 Ab increased the number of mTCR$^+$ T cells in the population.

TABLE 1

| Initial number of mTCR+ T cells | Total Number of cells following selective expansion | | |
|---|---|---|---|
| | 250 ng/mL H57 Ab | 500 ng/mL H57 Ab | 750 ng/mL H57 Ab |
| $1 \times 10^5$ | $1.59 \times 10^7$ | $2.02 \times 10^7$ | $2.96 \times 10^7$ |
| $5 \times 10^5$ | $4.34 \times 10^7$ | $4.94 \times 10^7$ | $4.89 \times 10^7$ |
| $10 \times 10^5$ | $4.76 \times 10^7$ | $6.02 \times 10^7$ | $6.06 \times 10^7$ |

TABLE 2

| Initial number of electroporated cells | Number of mTCR$^+$ T cells following selective expansion | | |
|---|---|---|---|
| | 250 ng/mL H57 Ab | 500 ng/mL H57 Ab | 750 ng/mL H57 Ab |
| $1 \times 10^5$ | $5.84 \times 10^6$ | $6.31 \times 10^6$ | $8.32 \times 10^6$ |
| $5 \times 10^5$ | $2.18 \times 10^7$ | $2.08 \times 10^7$ | $1.84 \times 10^7$ |
| $10 \times 10^5$ | $2.06 \times 10^7$ | $2.22 \times 10^7$ | $2.21 \times 10^7$ |

EXAMPLE 5

This example demonstrates that a second expansion with OKT3 Ab following a first expansion with H57 Ab further increases the number of mTCR$^+$ cells.

The electroporated cells which had already undergone selective expansion (i) at an initial number of $5\times10^5$ mTCR+ T cells with (ii) 250 ng/mL of H57 Ab, as described in Example 4 (referred to in this Example as "the first expansion"), were further expanded in a GREX flask (Wilson Wolf Manufacturing, St Paul, MN) using (i) the standard REP with OKT3 Ab, as described in Example 3 or (ii) H57 Ab, as described in Example 4 (referred to in this Example as "the second expansion").

Following the second expansion, the cells were stained with anti-CD3 antibody and anti-mTCRβ antibody (H57). The stained cells were counted by FACS. The FACS was gated on lymphocytes/PI(neg) cells. The results are shown in FIG. 7.

As shown in FIG. 7, a second expansion with OKT3 Ab following a first expansion with H57 Ab further increases the number of mTCR+ cells. The second expansion with the OKT3 Ab increased the number of mTCR+ cells to a greater extent as compared to the second expansion with the H57 Ab.

The percentage of viable cells, the total number of cells, the fold change in the number of cells achieved by the second expansion, the number of mTCR+ cells, and the fold change in mTCR+ cells achieved by the second expansion was also measured in the cells which underwent the second expansion with the OKT3 Ab and the H57 Ab and compared. The results are shown in Table 3. As shown in Table 3, a second expansion with OKT3 Ab following a first expansion with H57 Ab further increases the number of mTCR$^+$ cells. The second expansion with the OKT3 Ab increased the number of mTCR$^+$ cells to a greater extent as compared to the second expansion with the H57 Ab.

TABLE 3

| | $2^{nd}$ expansion with H57 | $2^{nd}$ expansion with OKT3 |
|---|---|---|
| Viability (%) | 97.7 | 98.3 |
| Total number of cells | $3.31 \times 10^9$ | $6.33 \times 10^9$ |
| Fold change in total number of cells | 331 | 1266 |
| Number of mTCR$^+$ cells | $6.38 \times 10^8$ | $2.40 \times 10^9$ |
| Fold change in number of mTCR$^+$ cells | 128 | 480 |

EXAMPLE 6

This example demonstrates that selectively expanding the number of T cells which express a mTCR increases the number of cells which express the mTCR.

PBL were transduced with a gammaretroviral vector encoding a murine F5 (mF5) anti-MART-1 TCR using standard methods on Day 0. On Day 10, transduced cells were prepared for secondary expansion. Expansion was carried out using (i) varying concentrations of IL-2, (ii) varying ratios of feeder cells, and (iii) either OKT3 Ab (30 ng/ml) or H57 Ab (50 ng/ml), as set forth in Table 4.

TABLE 4

| Cell | Mab | [IL-2] (CU) | Feeder Ratio |
|---|---|---|---|
| mF5 | sOKT3 | 500 | 200:1 |
| mF5 | sOKT3 | 50 | 200:1 |
| mF5 | mTCRb | 500 | 200:1 |
| mF5 | mTCRb | 50 | 200:1 |
| UTD | sOKT3 | 500 | 200:1 |
| UTD | sOKT3 | 50 | 200:1 |
| UTD | mTCRb | 500 | 200:1 |
| UTD | mTCRb | 50 | 200:1 |

The FACS plots in FIGS. 8A-8B show the percentages of untransduced and transduced cells expressing CD8 and the murine F5 (mF5) anti-MART-1 TCR prior to expansion with OKT3 Ab or H57 Ab (pre-rapid expansion protocol (REP)). The transduction efficiency prior to expansion was 83.9%. This transduced population was diluted in cell culture medium to approximately 5% murine TCR beta chain positive (mTCRb+) cells (FIG. 8C) prior to expansion.

The results following expansion of the number of cells in the 5% mTCRb+ starting population of FIG. 8C with (i) OKT3 (50 ng/ml) or H57 (50 ng/ml) in (ii) either 500 or 50 CU/IL-2 are shown in FIGS. 9 and 10A-10B. The number of cells expanded approximately 1500-2300-fold with OKT3 but did not show selective expansion of the number of cells in the mTCRb+ cell population. Alternatively, the number of cells expanded less (500-800-fold) with H57, however, they showed a 4-8-fold increase in the percentage of mTCRb+ cells. Overall, use of H57 in expansion resulted in more mTCRb+ cells.

EXAMPLE 7

This example demonstrates that selectively expanding the number of T cells which express a mTCR increases the number of cells which express the mTCR.

PBL were transduced with a retroviral vector encoding the murine F5 TCR as described in Example 6. The expression of CD8 and mTCRb by the transduced cells prior to expansion with H57 or OKT3 (starting cell population) is shown in FIGS. 11A-11C. The starting mTCR+ population originally had 64.7% mTCRb+ cells (FIG. 11B). The starting mTCR+ population was diluted four-fold to 14% mTCRb+ (FIG. 11C).

The number of transduced and UT cells was expanded with (i) no IL-2, 50 CU IL-2, or 500 CU IL-2 using (ii) OKT3 Ab or H57 Ab. The results are shown in FIGS. 12A-12E and 13A-13B.

After expansion, the OKT3 population did not show selective expansion of the overall mTCRb+ cell population with about equal percentages (5%) of CD8+ and CD8− transduced cells. In comparison, both H57-expanded populations (500 or 50 CU/IL-2, respectively) showed selective mTCRb+ expansion, at 31.2% and 59.1%, respectively. H57 expansion using 50 CU/IL-2 showed nearly 2-fold greater mTCRb+ cell expansion as compared to cells grown in 500 CU/IL-2.

As shown in FIGS. 13-13B, the numbers of cells expanded with OKT3 or H57 expanded approximately 1400-1600-fold in the presence of 500 CU/IL-2. However, H57 expansion plus 50 CU/IL-2 expanded about 3500-fold, more than twice that of the other conditions tested.

EXAMPLE 8

This example demonstrates that selectively expanding the number of T cells which express a mTCR increases the number of cells which express the mTCR.

PBL were transduced with a retroviral vector encoding the murine F5 TCR as described in Example 6. The expression of CD8 and mTCRb by the transduced cells prior to expansion with H57 or OKT3 (Pre-REP) is shown in FIGS. 14A-14F.

The numbers of transduced cells were expanded using (i) 50 CU IL-2 and (ii) OKT3 Ab (30 ng/ml) or H57 Ab (500, 50, 10, 5 ng/ml). The results are shown in FIGS. 14A-14F and FIG. 15. As shown in FIGS. 14A-14F and FIG. 15, the concentration of H57 antibody can be titrated down 10-fold without any detrimental effect on selective mTCRb+ expansion. Also, overall fold expansion was similar between all groups tested. A preferential expansion of CD8− cells following expansion with H57 was also observed.

EXAMPLE 9

This example demonstrates further expansion of the numbers of cells which underwent a first round of expansion with H57 in Example 8 with a second round of expansion with OKT3 or H57.

The mTCR-transduced cells which underwent expansion with H57 Ab in Example 8 were subjected to a second expansion with OKT3 or H57 to determine if further enrichment of mTCRb+ cells could be achieved. The expansion conditions were identical to those described in Example 8.

The results are shown in FIGS. 16A-16E and FIG. 17. A second expansion with OKT3 did not further enrich for mTCRb+ cells, but the number of cells did expand an additional 1000-fold. A second expansion with H57 did not add any additional enrichment for mTCRb+ cells and may have resulted in a slight decrease in mTCRb+ cells at 500 and 50 ng/ml. The fold expansion of the populations which underwent a second expansion with H57 was low, ranging from 200-500-fold.

EXAMPLE 10

This example demonstrates that mutation-specific TCRs are expressed by transposons on the day following electroporation.

As shown in FIG. 4A, autologous PBMC were obtained from healthy Donor 1 and healthy Donor 2 and cryopreserved. Cryopreserved PBMC were thawed and spun (200 g) at 20-23° C. for 10 minutes. The PBMC were placed in 50/50 media ($3\times10^6$ cells/mL) and cultured for 2 hours at 37° C. The SBTS plasmid encoding one of two mTCRs and a SBTS plasmid encoding transposase were electroporated into the autologous PBMC using an AMAXA NUCLEOFECTOR II device and kit (Lonza, Basel, Switzerland). The two mTCRs were (1) 4149-HUWE1-TCR1 (Class-I) and (2) 4149-TP53-TCRa2b2 (Class-II). Human T cell NUCLEOFECTOR solution (300 µL) contained the SBTS plasmid encoding the mTCR (45 µg) and the SBTS plasmid encoding transposase (15 µg). After the 2 hour rest period, non-adherent PBMC were collected by spinning (200 g) at 20-23° C. for 10 minutes, the media was removed and replaced with the human T cell NUCLEOFECTOR solution with SBTS plasmids (100 µL was added per cuvette). Electroporated cells were cultured in wells (5 mL 50/50 media/well) overnight at 37° C. After >18 hours, 50 U/mL benzonase was incubated at 37° C. for 1 hour. A mixed population of electroporated cells comprising cells which expressed the mTCR and cells which did not express the mTCR was obtained.

The day following electroporation, the electroporated cells were stained with (i) anti-CD3 Ab and (ii) anti-mTCRβ Ab. Unstained PBMC, untransfected PBMC, and PBMC electroporated with electroporation buffer only (Mock) (no TCR) served as negative controls. Expression of CD3 and the mTCR by the electroporated cells was measured by FACS (Gate: lymphocytes\live (PI-)). The results are shown in FIG. 18. As shown in FIG. 18, mutation-specific TCRs were expressed by transposons on the day following electroporation.

EXAMPLE 11

This example demonstrates that one round of expansion with H57 leads to selective outgrowth of the numbers of mTCR+ T cells.

PBMC from Donors 1 and 2 were electroporated as described in Example 10. As shown in FIG. 4A, after over 18 hours of culture at 37° C., the number of T cells expressing the murine TCR constant region (mTCR+ T cells) in the mixed population was selectively expanded. To selectively expand the number of mTCR+ T cells, the mTCR+ T cells ($5\times10^5$) were co-cultured with irradiated PBL ($1\times10^8$) in the presence of H57 Ab (Maine Biotechnology Services, Portland, ME) (250 ng/mL), IL-2 (50 IU/mL), and IL-21 (30 ng/mL).

The selectively expanded cells were stained and evaluated by FACS as described in Example 10. Unstained PBMC (FIG. 19A) and PBMC electroporated with electroporation buffer only (Mock) (no TCR) (FIG. 19B) served as negative controls. The results are shown in FIGS. 19A-19B. In FIGS. 19A-19B, the cell counts were determined on Day 14 after the one round of expansion with H57 from one T175 flask. As shown in FIGS. 19A-19B, one round of expansion with H57 led to selective outgrowth of the numbers of mTCR+ T cells.

EXAMPLE 12

This example demonstrates that further expansion of the numbers of cells which underwent a first round of expansion with H57 with a second round of expansion with OKT3 in gas permeable flasks results in large-scale expansion of the numbers of TCR-transposed T cells.

PBMC from Donors 1 and 2 were electroporated as described in Example 10. The numbers of transposed cells were selectively expanded with H57 antibody as described in Example 11. Following selective expansion of the numbers of mTCR$^+$ T cells, the numbers of mTCR$^+$ T cells were further expanded using the standard REP. In the standard REP, the selectively expanded mTCR$^+$ T cells (5×10$^6$) were co-cultured with irradiated PBL (5×10$^8$), OKT3 antibody (30 ng/mL), and IL-2 (3000 IU/mL).

The selectively expanded cells were stained and evaluated by FACS as described in Example 10. Unstained PBMC (FIG. 20A) and PBMC electroporated with electroporation buffer only (Mock) (no TCR) (FIG. 20B) served as negative controls. The cell counts on Day 14 after the standard REP from one GREX-100 gas peimeable flask (Wilson Wolf Corporation, St. Paul, MN) are shown in Table 5. The percentage of mTCR+ cells on Day 14 after the selective expansion with H57 are shown in Table 6.

TABLE 5

|  | 4149-HUWE1-TCR1 Cell count | 4149-TP53-TCRa2b2 Cell count |
| --- | --- | --- |
| Donor 1 | 1.2 × 10$^{10}$ cells | 1.2 × 10$^{10}$ cells |
| Donor 2 | 9.3 × 10$^9$ cells | 8.9 × 10$^9$ cells |

TABLE 6

|  | 4149-HUWE1-TCR1 % mTCR+ | 4149-TP53-TCRa2b2 % mTCR+ |
| --- | --- | --- |
| Donor 1 | 35.2% | 32.4% |
| Donor 2 | 76.8% | 84.3% |

The results are shown in FIGS. 20A-20B. As shown in FIGS. 20A-20B, further expansion of the numbers of cells which underwent a first round of expansion with H57 with a second round of expansion with OKT3 in gas permeable flasks resulted in large-scale expansion of the numbers of TCR-transposed T cells.

EXAMPLE 13

This example demonstrates that TCR-transposed T cells selectively expanded with the H57 antibody are specific for cognate mutated neoantigen.

PBMC from Donors 1 and 2 were electroporated as described in Example 10. The numbers of electroporated cells were selectively expanded with H57 antibody as described in Example 11. The 4149-HUWE1-TCR1 recognizes mutated HUWE1. The 4149-TP53-TCRa2b2 recognizes mutated TP53 (Y220C).

Immature DCs were pulsed with wild type (WT) HUWE1 peptide, mutated HUWE1 peptide, WT TP53, or mutated TP53. HUWE1 peptides were pulsed at 1 µg/mL. TP53 peptides were pulsed at 10 ng/mL. Co-cultures of 5×10$^4$ peptide-pulsed immature DCs and 10$^5$ T cells were incubated overnight at 37° C. DCs cultured alone and DCs pulsed with DMSO served as controls. IFN-γ secretion was measured by ELISA (enzyme-linked immunosorbent assay).

The results are shown in FIGS. 21A-21D. As shown in FIGS. 21A-21D, the TCR-transposed T cells selectively expanded with the H57 antibody recognized cognate mutated neoantigen.

EXAMPLE 14

This example demonstrates a method of selectively expanding the number of T cells which express a mTCR.

A schematic illustrating a method of electroporating PBMC with the mTCR and selectively expanding the number of mTCR T cells in accordance with an embodiment of the invention is shown in FIG. 22. As shown in FIG. 22, autologous PBMC were obtained from the patient and cryopreserved. Some of the PBMC were depleted of CD4+ cells with LD columns. The cryopreserved PBMC were thawed in complete media (CM) and spun at 175 g for 10 minutes at about 22° C. The cells were washed in Hank's balanced salt solution (HBSS) and counted. The cell count was 6×10$^7$.

As shown in FIG. 22, the SBTS plasmid encoding the mTCR (4149-HUWE1-TCR1 or 4149-TP53-TCRa2b2) and a SBTS plasmid encoding transposase were electroporated into the autologous PBMC using an AMAXA NUCLEOFECTOR II device and kit (Lonza, Basel, Switzerland). Human T cell NUCLEOFECTOR solution (300 µL) contained the SBTS plasmid encoding the mTCR (45 µg) and the SBTS plasmid encoding transposase (15 µg). This human T cell NUCLEOFECTOR solution was added to the cells and then the mixture of cells and DNA was added to the cuvettes (100 µL per cuvette).

As shown in FIG. 22, electroporated cells were cultured in wells (CM (5 mL), IL-2 (50 IU/mL), and IL-21 (30 ng/mL) per well) overnight at 37° C. After >18 hours, 50 U/mL benzonase was incubated at 37° C. for 1 hour. Cells were harvested, stained, and mTCR expression was measured by FACS. A mixed population of electroporated cells comprising cells which expressed the mTCR (mTCR+>1%) and cells which did not express the mTCR was obtained.

As shown in FIG. 22, after over 18 hours of culture at 37° C., the number of T cells expressing the murine TCR constant region (mTCR$^+$ T cells) in the mixed population was selectively expanded. To selectively expand the mTCR$^+$ T cells, the electroporated cells (5×10$^6$) were co-cultured with irradiated PBL (1×10$^8$) in the presence of H57 Ab (Maine Biotechnology Services, Portland, ME) (250 ng/mL), IL-2 (50 IU/mL), and IL-21 (30 ng/mL).

As shown in FIG. 22, the cells were cultured for 13 days. During this 13-day period, the cells were fed every 2-3 days with 50/50 CM with IL-2 (50 IU/mL), and IL-21 (30 ng/mL).

As shown in FIG. 22, mTCR+ cells were further enriched by contacting the cells with microbeads (Miltenyi Biotec, Bergisch Gladbach, Germany) conjugated with anti-biotin antibody and biotinylated H57 antibody in an LS column (Miltenyi Biotec).

Following enrichment of the mTCR+ cells with the H57-conjugated beads, the number of mTCR$^+$ T cells was further expanded using the standard REP. In the standard REP, the selectively expanded mTCR$^+$ T cells (5×10$^6$) were co-cultured with irradiated PBL (5×10⁸), OKT3 antibody (30 ng/mL), and IL-2 (3000 IU/mL). The timeline followed was as follows:

- day 0=electroporation (2×10⁷ total PBMC (TP53-TCR) or CD4-depleted PMBC (HUWE1-TCR))
- day 1=H57 REP (T175 flask; 5×10⁶ cells, 1×10⁸ irradiated PBMC, 250 ng/mL H57, 50 IU/mL IL-2, 30 ng/mL IL-21)
- day 14=H57 bead enrichment (H57-biotin mAb (GMP), CliniMACS biotin beads, LS columns)
- day 15=OKT3 REP (GREX-100 flask; 5e6 cells, 5e8 irradiated PBMC, 30 ng/mL OKT3, 3000 IU/mL IL-2)
- day 28=Harvest, phenotype, co-culture.

EXAMPLE 15

This example demonstrates the total number of cells and the percentage of CD3+mTCR+ cells obtained at four time points during the method described in Example 14.

The method described in Example 14 was carried out. The total number of cells in one cuvette and the percentage of CD3+mTCR+ cells in one cuvette were measured at four time points during the method described in Example 14: following electroporation, following selective expansion with H57, following enrichment with H57-conjugated beads, and following standard REP with OKT3.

Cells were left behind after the electroporation and the H57-conjugated bead enrichment. The counts were not adjusted to reflect theoretical yields but, rather, actual yields.

The results are shown in FIG. 23A (total number of cells) and FIG. 23B (percentage of CD3+mTCR+ cells).

EXAMPLE 16

This example demonstrates the percentage of mTCRβ+ cells measured at day 28 (post-OKT3 REP) of the method described in Example 14.

The method described in Example 14 was carried out. The percentage of mTCRβ+ cells was measured by FACS at day 28 (post-OKT3 REP). The results are shown in FIGS. 23C-23D. PBMC electroporated with electroporation buffer only (Mock) (no TCR) served as a negative control in FIGS. 23C-23D.

The percentage of CD4+ mTCRβ+ or CD8+mTCRβ+ cells was measured by FACS at day 28 (post-OKT3 REP). The results are shown in FIG. 23E.

EXAMPLE 17

This example demonstrates the memory cell phenotype of cells before (Day 1) and after (Day 28) expansion of the numbers of cells as described in Example 14.

The method described in Example 14 was carried out. The expression of memory phenotype markers was measured before (Day 1) or after (Day 28) expansion of the numbers of cells. The results are shown in FIGS. 24A-24D.

EXAMPLE 18

This example demonstrates the specificity of T cells following expansion of the numbers of cells as described in Example 14.

The method described in Example 14 was carried out. Immature DCs were pulsed with WT HUWE1 peptide, mutated HUWE1 peptide, WT TP53 peptide, or mutated TP53 peptide at a concentration of 10, 1, or 0.1 µg/mL. Co-cultures of peptide-pulsed immature DCs and transposed T cells were incubated overnight at 37° C. DCs pulsed with DMSO served as a control. IFN-γ secretion was measured by ELISA. The results are shown in FIGS. 25A-25B.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of selectively expanding a number of T cells, the method comprising:
modifying human T cells to express a TCR, wherein the TCR comprises a murine constant region;
producing a population of cells comprising a number of the human T cells expressing the TCR and a number of the human T cells not expressing the TCR;
culturing the population of cells in a first culture, wherein the first culture comprises (i) a first population of irradiated feeder cells, (ii) one or more cytokines, and (iii) a first antibody, or an antigen-binding portion thereof, wherein the first antibody, or antigen-binding portion thereof, specifically binds to the murine constant region of the TCR, wherein the first culture lacks a second antibody, or an antigen binding portion thereof, which specifically binds to the human CD3 complex, and wherein the first culture selectively expands the number of human T cells expressing the TCR over the number of human T cells not expressing the TCR.

2. The method according to claim 1, wherein the TCR has antigenic specificity for a cancer antigen.

3. The method according to claim 1, wherein the TCR has antigenic specificity for a viral antigen.

4. The method according to claim 1, wherein the one or more cytokines comprise one or more of IL-2, IL7, IL-12, IL-15, and IL-21.

5. The method according to claim 1, further comprising culturing the population of cells in a second culture, wherein the second culture comprises (i) a second population of irradiated feeder cells, wherein the second population of irradiated feeder cells comprise one or both of irradiated allogeneic feeder cells and irradiated autologous feeder cells, (ii) one or more cytokines, and (iii) the second antibody, or the antigen binding portion thereof, which specifically binds to the human CD3 complex.

6. The method according to claim 1, wherein the first antibody specifically binds to the murine constant region of the β chain of the TCR.

7. The method according to claim 1, wherein modifying human T cells to express the TCR comprises modifying the human T cells to express the TCR using transfection, transformation, transduction, electroporation, a transposon, a meganuclease, a zinc finger nuclease, a transcription activator-like effector nuclease (TALEN), or a clustered regularly interspaced short palindromic repeats (CRISPR)-Cas system.

8. The method according to claim 1, wherein the first antibody comprises the amino acid sequence of both of SEQ ID NO: 3 and SEQ ID NO: 4.

9. The method according to claim 1, wherein the method produces a selectively expanded population of cells, wherein about 10% to about 75% of the cells in the selectively expanded population express the TCR comprising the murine constant region.

10. The method according to claim 1, wherein the method produces a selectively expanded population of cells, wherein about 20% to about 99% of the cells in the selectively expanded population express the TCR comprising the murine constant region.

11. The method according to claim 1, comprising increasing the number of human T cells expressing the TCR comprising the murine constant region by about 10-fold to about 1,000-fold.

12. The method according to claim 1, wherein the TCR comprises a murine variable region.

13. The method according to claim 1, wherein the TCR comprises a human variable region.

14. The method of claim 1, further comprising separating the human T cells which express the TCR from the human T cells which do not express the TCR using the first antibody, or an antigen-binding portion thereof.

15. A method of treating or preventing a condition in a mammal, the method comprising:

preparing human T cells according to the method of any one of claims 1, 2-7, and 8-13; and administering the human T cells to the mammal in an amount effective to treat or prevent the condition in the mammal.

16. The method according to claim 15, wherein the condition is a viral condition.

17. The method according to claim 15, wherein the condition is cancer.

* * * * *